(12) United States Patent
Ueno

(10) Patent No.: US 6,452,039 B1
(45) Date of Patent: Sep. 17, 2002

(54) ENDOTHELIN ANTAGONIST

(76) Inventor: Ryuji Ueno, 7-29, Misaku-cho, Nishinomiya-shi, Hyogo 662-0038 (JP)

(*) Notice: Subject to any disclaimer, the term of this patent is extended or adjusted under 35 U.S.C. 154(b) by 0 days.

(21) Appl. No.: 09/475,285

(22) Filed: Dec. 30, 1999

Related U.S. Application Data

(62) Division of application No. 09/011,218, filed on Apr. 13, 1998, now Pat. No. 6,242,485.

(30) Foreign Application Priority Data

Jun. 10, 1996 (JP) .............................................. 8-147166
Jan. 23, 1997 (JP) .............................................. 9-010191

(51) Int. Cl.$^7$ ............................................ C07L 177/00
(52) U.S. Cl. ...................................... 560/121; 502/503
(58) Field of Search ........................... 560/121; 562/503

(56) References Cited

U.S. PATENT DOCUMENTS

| | | | | |
|---|---|---|---|---|
| 3,853,951 A | * | 12/1974 | Bernady et al. | |
| 3,974,195 A | * | 8/1976 | Youngdale | |
| 3,981,868 A | * | 9/1976 | Bernady et al. | |
| 4,018,811 A | * | 4/1977 | Schaub et al. | |
| 4,166,187 A | * | 8/1979 | Bundy | |
| 5,212,324 A | * | 5/1993 | Ueno | |
| 5,252,605 A | * | 10/1993 | Ueno | |
| 5,292,754 A | * | 3/1994 | Kishi et al. | |
| 5,346,921 A | * | 9/1994 | Ueno | |

FOREIGN PATENT DOCUMENTS

| | | | |
|---|---|---|---|
| EP | 0453433 | * | 7/1991 |
| EP | 0453127 | * | 10/1991 |
| EP | 0503887 | * | 9/1992 |
| FR | 2317915 | * | 2/1977 |

OTHER PUBLICATIONS

Tolstikov, G.A., Zh. Org. Khim. 26:119–127 (1990).*

* cited by examiner

*Primary Examiner*—Paul J. Killos
(74) *Attorney, Agent, or Firm*—Sughrue Mion, PLLC

(57) ABSTRACT

An endothelin antagonist comprising as the active ingredient a prostanoic acid derivative wherein the α-chain has eight or more skeletal carbon atoms.

6 Claims, No Drawings

ENDOTHELIN ANTAGONIST

This application is a divisional of Ser. No. 09/011,218 filed Apr. 13, 1998 now U.S. Pat. No. 6,242,485.

TECHNICAL FIELD

The present invention relates to a novel use of a prostanoic acid compound wherein the skeletal carbon atoms in α-chain are increased as endothelin antagonist.

The antagonist according to the present invention is useful as a treating agent for a variety of diseases participated of endothelin.

BACKGROUND ART

Endothelin is an endogenous bioactive peptide composed of 21 amino acids, and three types of which, i.e., endothelin-1, endothelin-2, and endothelin-3 are known.

Endothelin is a bioactive substance for continuously constricting vascular or non-vascular smooth muscle in direct or indirect way (regulation of release of a variety of endogenous substances), and production of endothelin increases due to lesion of endothelium. Excessive production of endothelin is considered-to be a cause for diseases such as hypertension, pulmonary hypertension, Buerger disease, primary Raynaud syndrome, asthma, eyegrounds (amphiblestrodes, chorioidea, and the like) diseases, diabetes, arterial sclerosis, renal failure, cardiac infarction, angina pectoris, cerebrovascular contraction, and cerebral infarction. Furthermore, it is known that endothelin is an important mediator with respect to multiple organ failures, and diseases such as disseminated intravascular coagulation due to endotoxin shock and the like as well as renal lesion induced by cyclosporin and the like. Moreover, it is also known that an endothelin concentration in blood increases after organ transplantation such as liver transplant.

Prostanoic acid is a skeletal compound constituting a common structural feature of natural prostaglandins (PG) groups and is represented by the following structural formula:

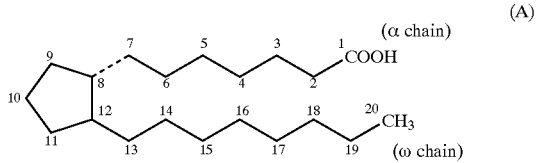

(A)

Natural PG groups are classified based on the structural feature of five-membered ring into PGA group, PGB group, PGC group, PGD group, PGE group, PGF group, PGG group, PGH group, PGI group, and PGJ group; and further they are classified as follows on the basis of presence or absence of unsaturation and oxidation at their chain portions:

numerical subscript 1 . . . 13,14-unsaturated-15-OH numerical subscript 2 . . . 5,6- and 13,14-di-unsaturated-15-OH numerical subscript 3 . . . 5,6,13,14- and 17,-18-tri-unsaturated-15-OH Moreover, the PGF group is classified into α (hydroxy group is in alpha-configuration) and β (hydroxy group is in beta-configuration) based on the configuration of hydroxy group at 9-position. In addition, a compound having oxo group in place of hydroxy group at 15-position is also known.

With respect to action of prostanoic acid compound on endothelin, it has been reported, for example, that $PGE_2$ inhibits renal endothelin inducible vasoconstriction in rat, and that prostacyclin ($PGI_2$) moderates renal endothelin inducible vasoconstriction in dog.

However, any of these prostanoic acid compounds is the one wherein the basic carbon atoms in α-chain are 7, and hence, they do not correspond to the prostanoic acid compound wherein the skeletal carbon atoms in α-chain increase.

U.S. Pat. No. 3,974,195 and European Patent Application Laid-Open No. 0453127 (corresponding to Japanese Patent Kokai Hei 5-58992) describe a compound wherein the skeletal carbon atoms in α-chain are increased by 2, but there is no description as to the action with respect to endothelin in these both publications.

DISCLOSURE OF THE INVENTION

An object of the present invention is to provide an endothelin antagonist useful for treating a variety of diseases and pathologies participated of endothelin.

The present inventor has eagerly studied with respect to biological activity of a prostanoic acid compound wherein the skeletal carbon atoms in α-chain are increased. As a result, it has been surprisingly found that a prostanoic acid compound wherein the skeletal carbon atoms in α-chain are increased has extremely strong antagonistic action as compared with that of a heretofore known prostanoic acid compound having 7 skeletal carbon atoms in α-chain, so that the present invention has been completed.

More specifically, the present invention provides an endothelin antagonist comprising a prostanoic acid compound having 8 or more skeletal carbon atoms in α-chain as an active ingredient.

As used herein, the term "a prostanoic acid compound having 8 or more skeletal carbon atoms in α-chain" includes any of substituted compounds and derivatives of a compound wherein the skeletal carbon atoms in α-chain of prostanoic acid are increased'so that the skeletal carbon atoms in α-chain are 8 or more, irrespective of the structure of five-membered ring, the number of double bond on α- or ω-chain, presence or absence of hydroxy group, oxo group, and the other substituents as well as any modification of chained portion.

Nomenclature of the prostanoic acid compounds herein uses the numbering system of the prostanoic acid represented in the formula (A) shown above.

While formula (A) shows a basic skeleton having twenty carbon atoms, the carbon atoms in the present invention are not limited thereto. Namely, the numbers of the carbons constituting the basic skeleton are assigned in such that number 1 is assigned to carboxylic acid, numbers 2 to 7 are given to the carbons on the α-chain in accordance with the order directing to the five-membered ring, numbers 8 to 12 are assigned to the carbons of the five-membered ring, and numbers 13 to 20 are given to the carbons on the ω-chain, respectively. However, in the case where carbon atoms decrease on the α-chain, numbers are successively deleted from the 2-position, while in the case where carbon atoms increase on the α-chain, nomenclature is made in such that the 2-position is substituted by any substituent in place of the carboxyl group (1-position). Likewise, in case of decreasing carbon atoms on the ω-chain, the number of carbon atoms is successively deleted from 20-position, while in case of increasing carbon atoms on the ω-chain, nomenclature is made in such that the carbon atoms at 21- and thereafter positions are considered to be substituents. Further, with respect to steric configuration, it is in accordance with that involved in the above indicated basic skeleton unless otherwise specified.

For instance, while PGD, PGE, and PGF mean compounds each containing hydroxy group(s) at 9-position and/or 11-position, the present invention includes also compounds containing any other group(s) in place of hydroxy group(s) at 9-position and/or 11-position. In case of nomenclature of these compounds, it is made in the form of 9-dehydroxy-9-substituted compound or 11-dehydroxy-11-substituted compound. In case of containing hydrogen in place of hydroxyl group, it is simply named as 9(11)-dehydroxy compound.

As mentioned above, while nomenclature of prostanoic acid compound is made on the basis of prostanoic acid skeleton in the present invention, when the above described compound has the same partial structure as that of prostaglandins, there is a case where an abbreviation of PG is also utilized for simplicity. In such case, a PG compound having two increased skeletal carbon atoms in α-chain, i.e., a PG compound having 9 skeletal carbon atoms in α-chain is named as 2-decarboxy-2-(2-carboxyethyl)-PG compound. Likewise, a PG compound having 11 skeletal carbon atoms in α-chain is named as 2-decarboxy-2-(4-carboxybutyl)-PG compound. Furthermore, a PG compound having two increased skeletal carbon atoms in ω-chain, i.e., a PG compound having 10 skeletal carbon atoms in ω-chain is named as 20-ethyl-PG compound. The naming may also be made based on IUPAC nomenclature. Examples of naming according to both the nomenclature are shown in the following Examples.

The prostanoic acid compounds used in the present invention are the ones wherein the skeletal carbon atoms in α-chain may be 8 or more, preferably 8 to 13, more preferably 9 to 13, and particularly preferably 9 to 11. Accordingly, any of the following compounds may be used, and they are, for example, $PG_1$ compounds having double bonds at 13–14 positions and a hydroxy group at 15-position, $PG_2$ compounds having further double bonds at 5–6 positions, $PG_3$ compounds having further double bonds at 17–18 positions, 15-keto-PG compounds having further an oxo group in place of hydroxy group at 15-position, 15-dehydroxy-PG compounds having hydrogen in place of hydroxy group at- 15-position, or either 13,14-dihydro-PG compounds wherein these double bonds at 13–14 positions are single bonds, or 13,14-didehydro-PG compounds wherein the double bonds at 13–14 positions are triple bonds. Moreover, examples of substituted compounds and derivatives include compounds wherein the terminal carboxyl group in α-chain of the above described prostanoic acid compound containing 8 or more skeletal carbon atoms in α-chain has been esterified, the physiologically acceptable salts thereof, compounds wherein the carbon atoms in ω-chain are increased, compounds having side chains (e.g., 1 to 3 carbon atoms) on α- and ω-chains, compounds having substituent(s) such as hydroxy, halogen, lower alkyl, hydroxy(lower)alkyl, and oxo, or double bond(s) on the five-membered ring, compounds having substituent(s) such as halogen, oxo, and aryl on α-chain, compounds having substituents such as halogen, oxo, hydroxy, lower alkoxy, lower alkanoyloxy, cyclo(lower)alkyl, aryl, and aryloxy on ω-chain, and compounds having substituent such as lower alkoxy, lower alkanoyloxy, cyclo(lower)alkyl, aryl, and aryloxy at the terminal of the ω-chain of which is shorter than that of normal prostanoic acid.

A preferred compound used in the present invention is represented by the formula (I):

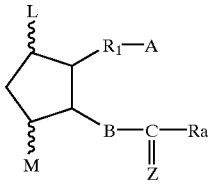

(I)

wherein L and M are hydrogen, hydroxy, halogen, lower alkyl, hydroxy(lower)alkyl, or oxo wherein at least one of L and M is a group other than hydrogen, and the five-membered ring may have at least one double bond;

A is —CH$_2$OH, —COCH$_2$OH, —COOH or its functional derivatives;

B is —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$—, or —CH$_2$—C≡C—;

Z is

wherein $R_4$ and $R_5$ are hydrogen, hydroxy, lower alkyl, or lower alkoxy wherein $R_4$ and $R_5$ are not hydroxy and lower alkoxy at the same time;

$R_1$ is a divalent saturated or unsaturated aliphatic hydrocarbon residue having 7 to 12 carbon atoms, which is unsubstituted or substituted by halogen, oxo, or aryl; and Ra is a saturated or unsaturated lower-medium aliphatic hydrocarbon residue which is unsubstituted or substituted by halogen, oxo, hydroxy, lower alkoxy, lower alkanoyloxy, cyclo(lower)alkyl, aryl, or aryloxy.

A group of particularly preferable compounds among the above described compounds is represented by the general formula (II):

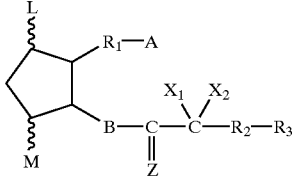

(II)

wherein L and M are hydrogen, hydroxy, halogen, lower alkyl, hydroxy(lower)alkyl, or oxo wherein at least one of L and M is a group other than hydrogen, and the five-membered ring may have at least one double bond;

A is —CH$_2$OH, —COCH$_2$OH, —COOH or its functional derivatives;

B is —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$—, or —CH$_2$—C≡C—;

Z is

 or 

wherein $R_4$ and $R_5$ are hydrogen, hydroxy, lower alkyl, or lower alkoxy wherein $R_4$ and $R_5$ are not hydroxy and lower alkoxy at the same time;

$X_1$ and $X_2$ are hydrogen, lower alkyl, or halogen;

$R_1$ is a divalent saturated or unsaturated aliphatic hydrocarbon residue having 7 to 12 carbon atoms, which is unsubstituted or substituted by halogen, oxo, or aryl;

$R_2$ is a single bond or lower alkylene; and $R_3$ is lower alkyl, lower alkoxy, cyclo(lower)alkyl, aryl, or aryloxy.

Furthermore, the present invention relates to a compound represented by the general formula (III):

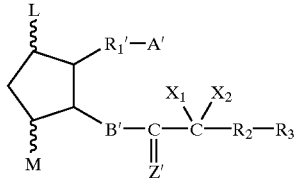 (III)

wherein L and M are hydrogen, hydroxy, halogen, lower alkyl, hydroxy(lower)alkyl, or oxo wherein at least one of L and M is a group other than hydrogen, and the five-membered ring may have at least one double bond;

A' is —COOH, or its functional derivatives;

B' is —$CH_2$—$CH_2$—, or —CH=CH—;

Z' is

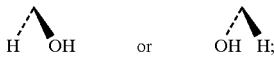

X1 and $X_2$ are hydrogen, lower alkyl, or halogen wherein at least one of $X_1$ and $X_2$ is a halogen;

$R_1$ is a divalent saturated or unsaturated aliphatic hydrocarbon residue having 8 carbon atoms, which is unsubstituted or substituted by halogen, oxo, or aryl;

$R_2$ is a single bond or lower alkylene; and $R_3$ is lower alkyl, lower alkoxy, cyclo(lower)alkyl, aryl, or aryloxy.

Moreover, the present invention relates to a compound represented by the general formula (IV):

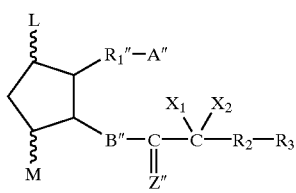 (IV)

wherein L and M are hydrogen, hydroxy, halogen, lower alkyl, hydroxy(lower)alkyl, or oxo wherein at least one of L and M is a group other than hydrogen, and the five-membered ring may have at least one double bond;

A" is —COOH, or its functional derivatives;

B" is —$CH_2$—$CH_2$—, or —CH=CH—;

Z" is

$X_1$ and $X_2$ are hydrogen, lower alkyl, or halogen;

$R_1$" is a divalent saturated or unsaturated aliphatic hydrocarbon residue having 8 carbon atoms, which is unsubstituted or substituted by halogen, oxo, or aryl;

$R_2$ is a single bond or lower alkylene; and $R_3$ is lower alkyl, lower alkoxy, cyclo(lower)alkyl, aryl, or aryloxy.

Still further, the present invention relates to a compound represented by the general formula (V):

(V)

wherein L and M are hydrogen, hydroxy, halogen, lower alkyl, hydroxy(lower)alkyl, or oxo wherein at least one of L and M is a group other than hydrogen, and the five-membered ring may have at least one double bond;

A'" is —COOH, or its functional derivatives;

B'" is —$CH_2$—$CH_2$—, or —CH=CH—;

Z'" is $X_1$ and $X_2$ are hydrogen, lower alkyl, or halogen;

$R_1$'" is a divalent saturated or unsaturated aliphatic hydrocarbon residue having 10 carbon atoms, which is unsubstituted or substituted by halogen, oxo, or aryl;

$R_2$ is a single bond or lower alkylene; and $R_3$ is lower alkyl, lower alkoxy, cyclo(lower)alkyl, aryl, or aryloxy.

In the above described formula, the term "unsaturated" appeared in $R_1$, $R_1$', $R_1$", $R_1$'", and Ra means to include at least one or more of double bond(s) and/or triple bond(s) isolatedly, separately, or serially present between carbon atoms of the straight or side chain.

The term "lower-medium aliphatic hydrocarbon" means a hydrocarbon having a straight chain of 1 to 14 carbon atoms which may have side chain (wherein the side chain has preferably 1 to 3 carbon atoms), and preferably, 1 to 9 carbon atoms.

The term "aliphatic hydrocarbon having 7 to 12 carbon atoms" means a hydrocarbon having a straight chain of 7 to 12 carbon atoms which may have side chain (wherein the side chain has preferably 1 to 3 carbon atoms). Preferable is such that the hydrocarbon has 8 to 12 carbon atoms, and particularly preferable is such that the hydrocarbon has 8 to 10 carbon atoms.

The term "halogen" includes fluorine, chlorine, bromine, and iodine.

The term "lower" means a group having 1 to 6 carbon atoms unless otherwise specified.

The term "lower alkyl" means a straight- or branched-chain saturated hydrocarbon group having 1 to 6 carbon atoms, for example, methyl, ethyl, propyl, isopropyl, butyl, isobutyl, t-butyl, pentyl, and hexyl.

The term "lower alkoxy" means a lower alkyl-O— wherein the lower alkyl is as described above.

The term "hydroxy(lower)alkyl" means an alkyl as described above, which is substituted by at least one hydroxy group, for example, hydroxymethyl, 1-hydroxyethyl, 2-hydroxyethyl, and 1-methyl-1-hydroxyethyl.

The term "lower alkanoyloxy" means a group represented by the formula RCO—O— wherein RCO— is an acyl formed by oxidation of a lower alkyl as described above, for example, acetyl.

The term "lower cycloalkyl group" means a group formed by cyclization of a lower alkyl group containing 3 or more carbon atoms as described above, for example, cyclopropyl, cyclobutyl, cyclopentyl, and cyclohexyl.

The term "aryl" includes aromatic hydrocarbon rings or heterocyclic groups (preferably monocyclic groups) which may be substituted, for example, phenyl, tolyl, xylyl, and thienyl. An example of the substituent in this case includes halogen, and halogen substituted lower alkyl group (wherein halogen atom and lower alkyl group are as described above).

The term "aryloxy" means a group represented by the formula ArO— (wherein Ar is an aryl group as described above).

The term "functional derivatives" of the carboxy group represented by A includes salts (preferably pharmaceutically acceptable salts), esters, and amides.

Examples of suitable "pharmaceutically acceptable salts" include nontoxic salts which are commonly used, and they are salts with inorganic bases, for example, alkali metal salts (sodium salt, potassium salt and the like); alkaline earth salts (calcium salt, magnesium salt and the like); ammonium salts; salts with organic bases, for example, amine salts (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, lysine salt, procaine salt, and caffeine salt); basic amino acid salts (such as arginine salt, and lysine salt); tetraalkyl ammonium salts and the like. These salts may be manufactured from, for example, corresponding acids and bases in accordance with a conventional manner or salt exchange.

The esters includes aliphatic esters, for example, lower alkyl esters such as methyl ester, ethyl ester, propyl ester, isopropyl ester, butyl ester, isobutyl ester, t-butyl ester, pentyl ester, and 1-cyclopropylethyl ester; lower alkenyl esters such as vinyl ester, and allyl ester; lower alkynyl esters such as ethynyl ester, and propynyl ester; hydroxy (lower)alkyl esters such as hydroxyethyl ester; and lower alkoxy(lower)alkyl esters such as methoxymethyl ester, and 1-methoxyethyl ester as well as, for example, optionally substituted aryl esters such as phenyl ester, tosyl ester, t-butylphenyl ester, salicyl ester, 3,4-dimethoxyphenyl ester, and benzamidephenyl ester; and aryl(lower)alkyl esters such as benzyl ester, trityl ester, and benzhydryl ester. An example of amides includes mono- or di-lower alkyl amides such as methylamide, ethylamide, and dimethylamide; aryl amides such as anilide, and toluidide; and alkyl or aryl sulfonyl amides such as methylsulfonyl amide, ethylsulfonyl amide, and tolylsulfonyl amide.

A preferred example of A-group includes —COOH, —COOCH$_3$, —COOCH$_2$CH$_3$, —COOCH(CH$_3$)$_2$, and —CONHSO$_2$CH$_3$.

In the above described formula (I), configurations of the ring, α- and/or ω-chain(s) may be the same with or different from those of natural prostaglandins group. However, it is to be noted that the present invention includes also the mixtures of compounds having natural and nonnatural configurations.

An example of the typical compounds according to the present invention includes 2-decarboxy-2-(carboxy lower alkyl)-PG compounds, particularly 2-decarboxy-2-(2-carboxyethyl)-PG compound, 2-decarboxy-2-(4-carboxybutyl)-PG compound, 5-fluoro-form, 6-keto-form, 11-dehydroxy-form, 16-fluoro-form, 16-methyl-form, 17-fluoro-form, 17-methyl-form, 18-methyl-form, 19-methyl-form, 20-methyl-form, 20-ethyl-form, 20-propyl-form, 18,19,20-trinor-17-phenyl-form and the like.

In the PG compounds used in the present invention, when 13-,14-positions are saturated and 15-position is oxo (i.e., in case of 13,14-dihydro-15-keto-form), there is a case where keto-hemiacetal equilibrium occurs as a result of formation of hemiacetal between the hydroxy at 11-position and the keto at 15-position.

In the case when such tautomers exist, a ratio of existence of both the tautomers are depend upon the structure of the other party or the types of substituents, and according to circumstances, either of tautomers exists predominantly. However, the present invention includes these both tautomers, and there is a case where a compound is indicated in accordance with either keto-form structural formula or nomenclature irrespective of presence or absence of such tautomers. In other words, this is only a manner for conveniences' sake, and there is no intention of excluding hemiacetal-form compounds.

In the present invention, any of the individual tautomers, the mixture thereof, or optical isomers, the mixtures thereof, racemic modifications, and other isomers such as stereoisomers may be used for the same purpose.

While the compounds according to the present invention can be manufactured by a variety of methods, they may also be manufactured, for example, in accordance with the following Synthetic Chart. In the following Synthetic Chart, P$_1$, P$_2$, P$_3$, P$_4$, P$_5$, P$_6$, and P$_7$ are protective groups, and X$_1$, X$_2$, R$_2$, and R$_3$ are as described above.

Synthetic Chart 1

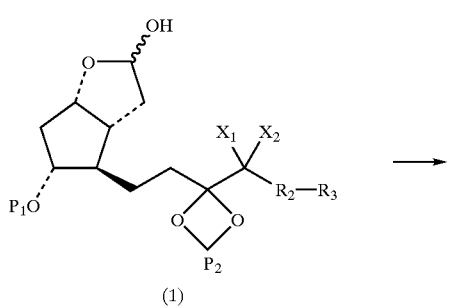

(1)

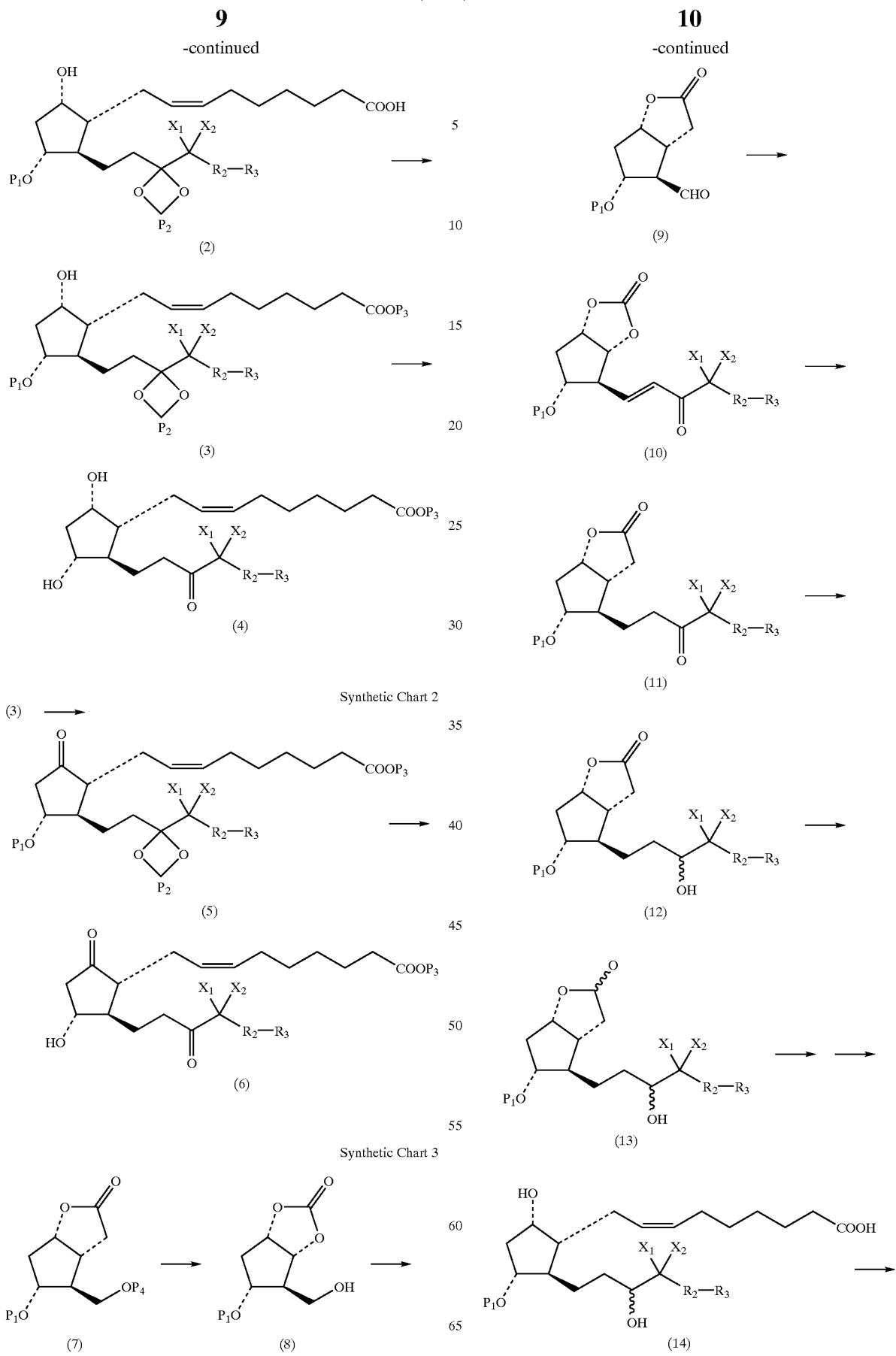

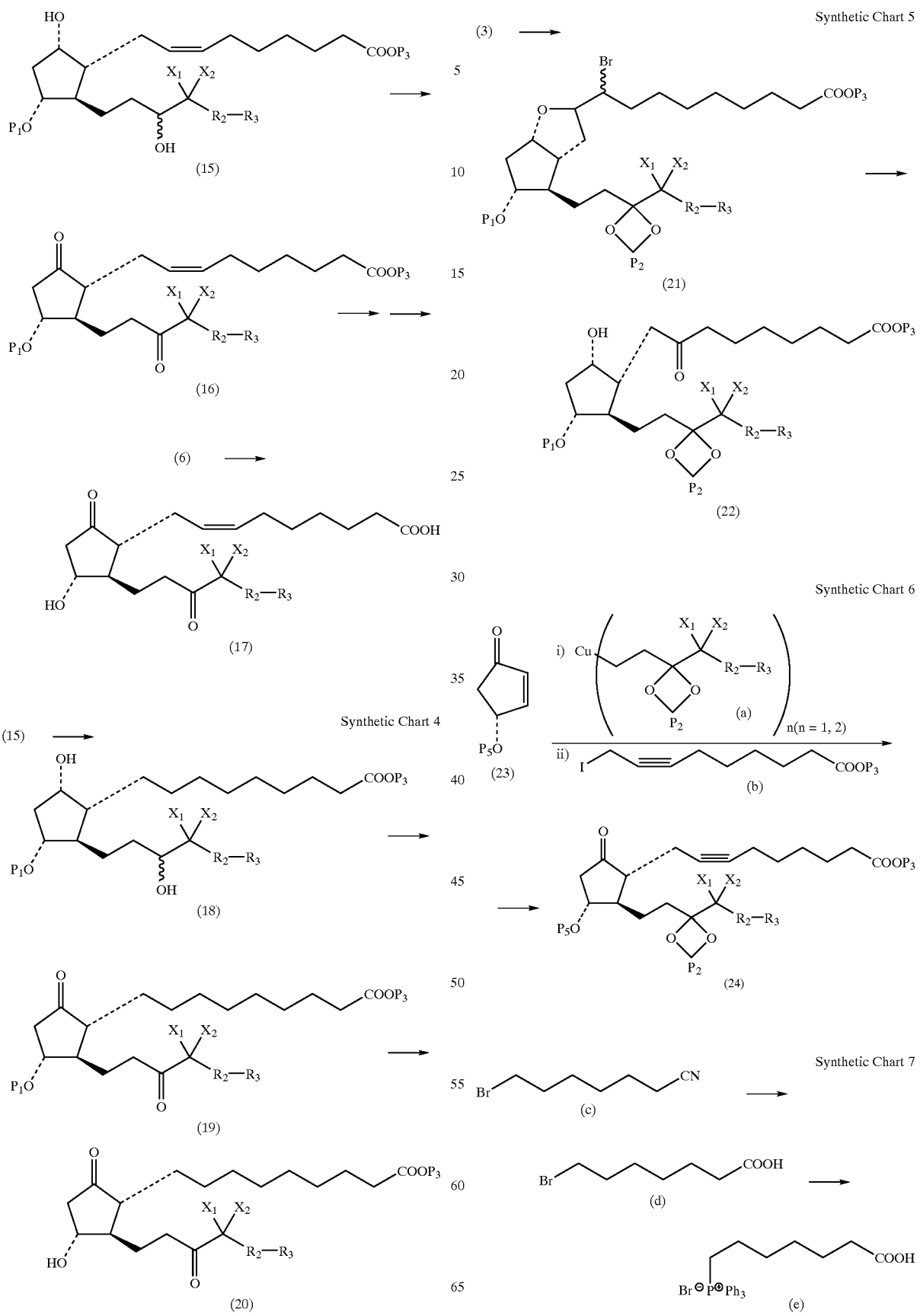

Synthetic Chart 8

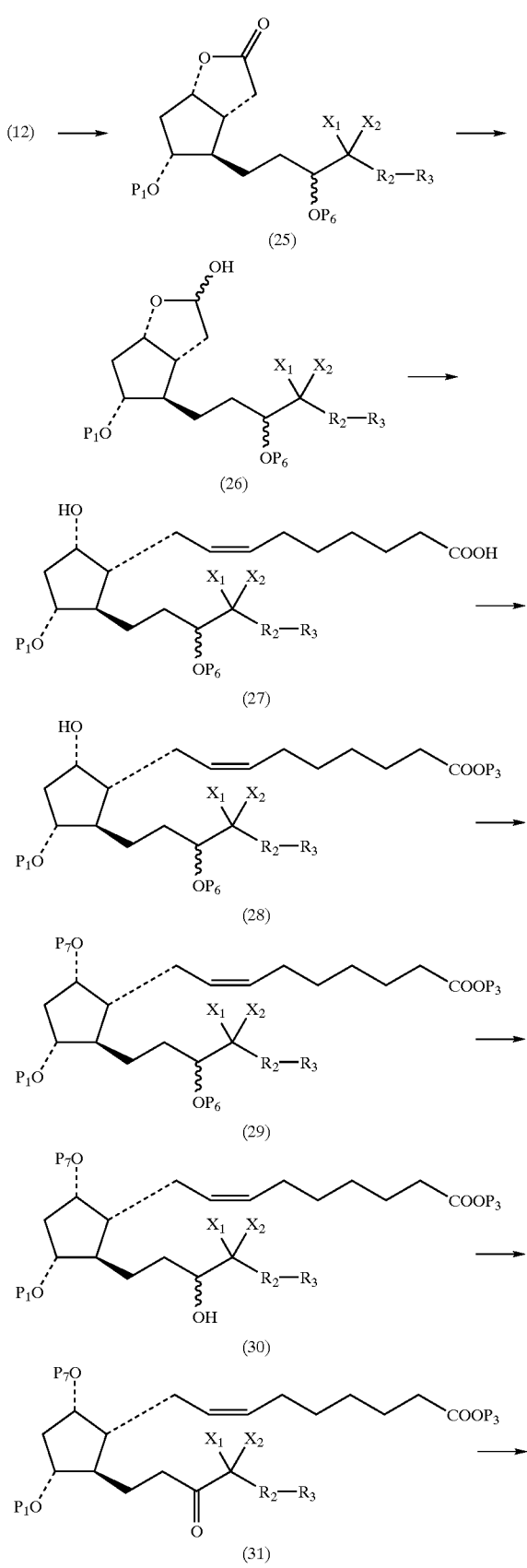

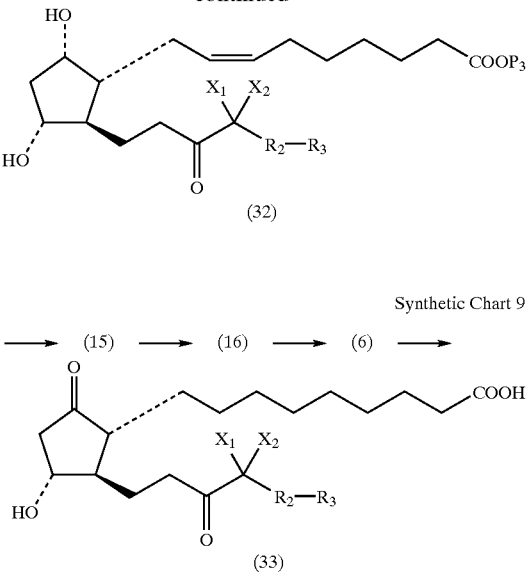

Synthetic Chart 9

In the Synthetic Chart 1, with the compound (1) (wherein, for example, when $X_1$ and $X_2$ are hydrogens, respectively, the resulting compound corresponds to the Compound 8 shown in the Synthesis Chart I in page 37 of Japanese Patent Kokai Sho 64-52753) is reacted ylide obtained from (6-carboxyhexyl)triphenyl phosphonium bromide to produce the compound (2), it is esterified to obtain the compound (3), and the protective groups are removed therefrom to obtain the target compound (4). Furthermore, in the Reaction Formula 2, the above described compound (3) is subjected to Jones oxidation to prepare the compound (5), and from which are removed the protective groups to obtain the compound (6).

As another example, in the Synthetic Chart 3, the compound (8) prepared from the compound (7) (commercially available product) as a result of removing a protective group is subjected to Swan oxidation to produce the aldehyde-form (9), and with which is reacted 2-oxoheptyl phosphonate (e.g., 3,3-dihalo-form) to obtain the compound (10). The resulting compound (10) is catalytically reduced to prepare the compound (11), the ketone thereof is reduced with sodium hydrogenated boron to produce the compound (12), and is reduced with hydrogenated diisobutyl aluminum to obtain lactol (13). With which is reacted carboxyhexyl phosphonium bromide to prepare the compound (14), esterified to produce the compound (15), oxidized to produce the compound (16), and from which is removed a protective group to obtain the compound (6). If desired, the protective group for carboxyl group is removed to obtain the free acid (17). Moreover, in the Synthetic Chart 4, the above described compound (15) is catalytically reduce to prepare the compound (18), it is subjected to Swan oxidation to produce the compound (19), and from which is removed a protective group, whereby the target compound (20) can be obtained.

In the above described manufacturing methods, when the reduction by which the compound (1) is obtained from the compound (10) is omitted, a compound wherein B is —CH=CH— is obtained.

In the general formula (I), when such compound is a target compound wherein M is a group other than OH (for example, a lower alkyl), lactone of the compound (12) wherein 11-position is released from the protection, while 15-position is protected is reduced to lactol, into which is introduced α-chain in accordance with Wittig reaction, the hydroxy group at 11-position is protected by, for example, a lower alkane or a monocyclic aryl sulfonic acid group, then, is oxidized (for example, Jones oxidation) to obtain 10-en-9-on, and with which is reacted, for example, a lower alkyl copper complex to prepare 11-lower alkyl-form. PGD-type compounds are obtained by oxidation of the 11-nonprotective form, while PGA-type compounds are obtained from the 10-en-9-on form. Furthermore, 6-keto compound is obtained in such a manner, for example, as shown in the Synthetic Chart 5 that N-bromsuccinimide or iodine is reacted with the compound (3) to produce the compound (21), and the resulting compound is treated with DBU. 5,6-dehydro compound (i.e., acetylene-form) is obtained in such a manner, for example, as shown in the Synthetic Chart 6 that with a copper enolate prepared by reacting a copper complex with the compound (23) is reacted 8-alkoxycarbonyl-1-iodo-2-octine. A saturated α-chain introducing agent is manufactured, for example, in accordance with the Synthetic Chart 7.

Furthermore, as another example, in the Synthetic Chart 8, the hydroxyl group at 15-position of the compound (12) is protected (by, for example, a silyl protective group) to prepare the compound (25), the lactone is reduced to lactol to obtain the compound (26), and with which is reacted an a-chain introducing agent, for example, an ylide prepared from (6-carboxyhexyl)triphenyl phosphonium bromide to obtain the compound (27). Then, the carboxyl group is protected to obtain the compound (28), the hydroxyl group at 9-position thereof is protected to prepare the composition (29), from the 15-position thereof the protective group is removed to obtain the compound (30), oxidized to produce the compound (31), and then, when from the 9- and 11-positions thereof are removed the protective groups, the target compound (32) is obtained.

Moreover, in the Synthetic Chart 9, the compound (14) in the Synthetic Chart 3 is protected by a protective group which can be removed by catalytic reduction (for example, benzyl) to prepare the compound (15), the 9-position thereof is oxidized, then, from the 11-position thereof is removed the protective group to obtain the compound (6), and when the resulting compound is catalytically reduced, a target compound (33) is obtained.

The above described prostanoic acid compounds containing 8 or more carbon atoms in α-chain are useful as endothelin antagonist.

The compounds used in the present invention may be utilized as a pharmaceutical for animal and human being, and they may usually be administered systemically or locally in accordance with ophthalmic administration, oral administration, intravenous injection (including drip infusion), subcutaneous injection, intrarectal administration and the like manner. Especially, use in the form of eye drops is useful. Although the dosage varies dependent upon type, age, body weight, symptom to be treated, desired therapeutic effect, administration route, period to be treated or the like of objects such as animal or human being and the like, sufficient effect is ordinarily achieved by usually the dosage of 0.01 to 100 μg/eye in case of local administration, or the dosage of 0.001 to 500 mg/kg in case of systemical administration in accordance with divided dose into two to four fractions per day or under sustained condition.

The ophthalmic preparations according to the present invention include ophthalmic solution or ophthalmic ointment and the like. Ophthalmic solution is prepared by either dissolving the active ingredient into sterile aqueous solution, for example, physiological saline, buffer solution and the like, or combining the former with the latter used at the time of administration. The ophthalmic ointment is prepared by mixing the active ingredient with a base.

The solid composition for oral administration used according to the present invention includes tablet, troche, sublingual tablet, capsule, pill, powder, granule and the like. In such a solid composition, one or more active ingredient(s) is (are) admixed with at least one inactive diluent such as lactose, mannitol, glucose, hydroxypropyl cellulose, microcrystalline cellulose, starch, polyvinyl pyrrolidone, magnesium aluminate metasilicate. According to a conventional procedure, a composition may contain additives other than the inactive diluent, for example, lubricant such as magnesium stearate; disintegrator such as cellulose calcium gluconate; and stabilizer, for example, etherificated cyclodextrin such as α, β, and γ-cyclodextrin, or dimethyl-α-, dimethyl-β-, trimethyl-β-, and hydroxypropyl-β-cyclodextrin, branched cyclodextrin such as glycosyl-, maltosyl-cyclodextrin, formilated cyclodextrin, sulfur-containing cyclodextrin, misoprotol (phonetic), and phospholipid. When any of the above described cyclodextrin is used, there is a case where a clathrate inclusion compound is formed from the cyclodextrin to increase the stability of a composition. Furthermore, there is a case when liposome is formed by utilizing phospholipid, the stability of the resulting product increases. If desired, tablet or pill may be covered or coated with a film or two or more layers made of a substance soluble in ventriculus or intestine such as saccharose, gelatin, hydroxypropyl cellulose, and hydroxypropyl methyl cellulose phthalate. Furthermore, a composition may be formed in capsule by the use of a disintegrable material such as gelatin. In case of requiring fast-acting property, a composition may be formed in sublingual tablet.

As a base, glycerin, lactose and the like may be used. An example of liquid compositions for oral administration includes emulsion, solution, suspension, syrup, and elixir formulations. They may contain an inactive diluent used ordinarily such as purified water, and ethanol. Any of these compositions may further contain an additive such as wetting agent, and suspending agent; edulcorant; flavoring material, aromatic, and preservative in addition to the inactive diluents.

As another composition for oral administration, there is a spraying agent containing one or more active ingredient(s) and being formulated in accordance with a manner which itself has been well known.

An example of parenteral solutions according to the present invention includes sterile aqueous or nonaqueous solution, suspension, and emulsion. An example of media for the aqueous solution and the suspension includes distilled water for injection, physiological saline, and Ringer solution.

An example of diluent for the nonaqueous solution and the suspension includes propylene glycol, polyethylene glycol, vegetable oils such as olive oil, alcohols such as ethanol, polysorbate and the like. These compositions may further contain adjuvants such as preservative, wetting agent, emulsion, and dispersant. They are sterilized by, for example, filtration passing them through a bacteria remaining filter, incorporation of a bacteriocide, gas sterilization, or radiation sterilization. They may also be manufactured in the form of a sterile solid composition, and it is dissolved in sterile water or a sterile solvent for injection prior to the application therefor.

Another form for such compositions is suppository or vaginal suppository. These suppositories may be prepared by admixing an active ingredient with a base such as cacao butter or the like which softens at body temperature, and in this case, a nonionic surfactant having a suitable softening temperature may be added further to improve the absorption thereof.

EXAMPLE

Although the present invention will be explained in detail by the following examples of syntheses and tests, they do not limit the invention.

Synthesis Example 1

Preparation of 2-decarboxy-2-(2-carboxyethyl)-13,14-dihydro-15-keto-20-ethyl-PGF$_2\alpha$ isopropyl ester [IUPAC name:isopropyl (Z)-9-[(1R,2R,3R,5S)-3,5-dihydroxy-2-(3-oxodecyl)cyclopentyl]-7-nonenoate](4-a)

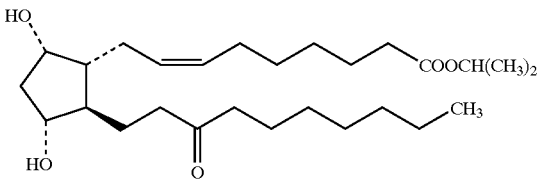

(4-a)

Preparation of Raw Material Compound (6-carboxyhexyl)triphenylphosphonium bromide (e)

7-Bromoheptane nitrite (c) (10.0 g) was added to 40% hydrobromic acid (80 ml), and refluxed for 6 hours. The product was extracted with ether after dilution with water. The crude product obtained by the conventional treatment was purified on the silica gel column to give 7-bromoheptanoic acid(d) [yield:7.60 g (69%)].

(6-Carboxyhexyl)triphenylphosphonium bromide(e) was obtained from 7-bromoheptanoic acid(d) (7.60 g) and triphenylphosphine (10.0 g) [yield:16.0 g (93%)].

Preparation of Object Compound 1-1)(Z)-9-[(1R,2R,3R,5S)-2-(3,3-ethylene dioxydecyl)-5-hydroxy-3-tetrahydropyranyloxy)cyclopentyl]-7-nonenoic acid(2-a)

Dimethyl sulfoxide (DMSO)(10 ml) was added to sodium hydride (60%;0.422 g) which was washed with hexane under argon atomosphere, and the mixture was maintained at 60° C. for 3 hours and then cooled to room temperature. (6-Carboxyhexyl)triphenyl-phosphonium bromide (2.49 g) was added to the mixture and the resultant mixture was agitated for 30 minutes. The solution of [1S,3(R,S),5R,6R,7R]-6-(3,3-ethylene dioxydecyl)-7-tetrahydropyranyloxy-2-oxabicyclo[3.3.0]ortane-3-ol (1-a) in DMSO (11 ml) was added to the reaction mixture. The resultant mixture was agitated at room temperature for 2 hours and at 45° C. for 1 hour, and then ice-water was poured into the reaction mixture. The titled compound (2-a) was obtained by the conventional treatment of the reaction mixture (yield:1.68 g).

1-2)Isopropyl (Z)-9-[(1R,2R,3R,5S)-2-(3,3-ethylene dioxydecyl)-5-hydroxy-3-(tetrahydropyranyloxy) cyclopentyl]-7-nonenoate (3-a)

The compound (2-a)(1.68 g) in acetonitrile (15 ml) was esterified with 1,8-diazabicyclo[5.4.0]-7-undecene (DBU) (0.78 ml) and isopropyl iodide (0.35 ml) by the conventional manner to give the titled compound (3-a). The product was purified on silica gel column (yield:0.908 g(88%)).

1-3)Isopropyl (Z)-9-[(1R,2R,3R,5S)-3,5-dihydroxy-2-(3-oxodecyl)cyclopentyl]-7-nonenoate (4-a)

The compound (3-a)(0.305 g) was dissolved in the solvent mixture (acetic acid:THF:water=2:1:1)(6 ml) and the solution was maintained at 50° C. for 14 hours. The crude product obtained by the conventional treatment was purified on silica gel column to give the titled compound (4-a) [yield:0.213 g(90%)].

Compound (4-a)[compound (4) wherein $X_1=X_2=H$, $R_2-R_3$=hexyl, $P_3$=isopropyl]

NMR(CDCl$_3$) δ: 0. 85(t, 3H, J=6.5 Hz), 1.20(d, 6H, J=6 Hz), 1.23~2.65(m, 34H), 3.86(m, 1H), 4.16(m, 1H), 4.99 (Hept, 1H, J=6 Hz), 5.39(m, 2H)

Synthesis Example 2

Preparation of 2-decarboxy-2-(2-carboxyethyl)-13,14-dihydro-15-keto-20-ethyl-PGE$_2$ isopropyl ester [IUPAC name:isopropyl (Z)-9-[(1R,2R,3R)-3-hydroxy-5-oxo-2-(3-oxodecyl)cyclopentyl]-7-nonenoate] (6-a)

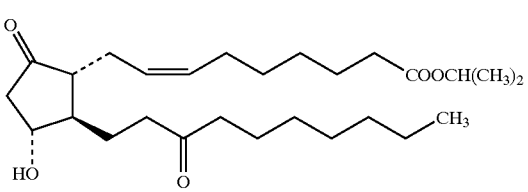

(6-a)

2-1)isopropyl (Z)-9-[(1R,2R,3R)-2-(3,3-ethylene dioxydecyl)-5-oxo-3-(tetrahydropyranyloxy)cyclopentyl]-7-nonenoate (5-a)

Oxalyl chloride (2M; 0.45 ml) and DMSO(0.13 ml) were added to dichloromethane (5 ml) which was previously cooled to −70° C. and the mixture was agitated for 15 minutes. The solution of isopropyl (Z)-9-[(1R,2R,3R,5S)-2-(3,3-ethylene dioxydecyl)-5-hydroxy-3-(tetrahydropyranyloxy)cyclopentyl]-7-nonenoate (3-a) (0.350 g) in dichloromethane (7 ml) was dropped into the mixture. The resultant mixture was warmed to −55° C. and agitated for 15 minutes, and then triethylamine (0.25 ml) was added to the mixture. The resultant mixture was warmed to 10° C. over 6 hours. The crude product obtained by the conventional treatment of the reaction mixture was purified on silica gel column to give the titled compound (5-a) [yield:0.311 g(89%)].

2-2)isopropyl (Z)-9-[(1R,2R,3R)-3-hydoxy-5-oxo-2-(3-oxodecyl)cyclopentyl]-7-nonenoate (6-a)

The compound (5-a)(0.311 g) was dissolved in the solvent mixture (acetic acid:THF:water=2:1:1)(5 ml) and the solution was maintained at 50° C. for 3 hours. The crude product obtained by the conventional treatment of the reaction mixture was purified on silica gel column to give the titled compound (6-a)[yield:0.156 g(66%)].

Compound (6-a) [compound (6) wherein $X_1=X_2=H$, $R_2-R_3$=hexyl, $P_3$=isopropyl]

NMR(CDCl$_3$) δ: 0.86(t, 3H, J=6.5 Hz), 1.20(d, 6H, J=6 Hz), 1.23~2.75(m, 33H), 4.20(m, 1H), 4.99(Hept, 1H, J=6 Hz),5.15~5.50(m, 2H)

Synthesis Example 3

Preparation of 2-decarboxy-2-(2-carboxyethyl)-13,14-dihydro-15-keto-16,16-difluoro-PGE$_2$ [IUPAC name:(Z)-9-[(1R,2R,3R)-2-(4,4-difluoro-3-oxooctyl)-3-hydroxy-5-oxocyclopentyl]-7-nonenoic acid](17-a)

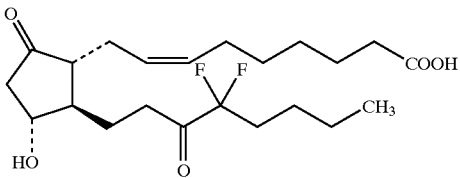

(17-a)

3-1) (1S,5R,6R,7R)-6-(4,4-difluoro-3-oxooctenyl)-7-tetrahydropyranyloxy)-2-oxabicyclo[3,3,0]octane-3-one (10-a)

(1S,5R,6R,7R)-6-Hydroxymethyl-7-(tetrahydropyranyloxy)-2-oxabicyclo[3,3,0]octane-3-one (8-a) (27.8 g) prepared from the commercially available (1S,5R,6R,7R)-6-(t-butyldimethyl silyloxymethyl)-7-(tetrahydropyranyloxy)-2-oxabicyclo[3,3,0]octane-3-one (7-a) was subjected to Swan oxidation with oxalyl chloride (2.0 M;109.3 ml), DMSO (31.0 ml) and triethylamine (150 ml) in dichloromethane (800 ml) to give the compound (9-a) (P$_1$=tetrahydropyranyl).

The compound (9-a) was reacted with dimethyl-3,3-difluoro-2-oxoheptylphosphonate (30.0 g) in dichloromethane in the presence of thallium methoxide (8.23 ml). The crude product obtained by the conventional treatment of the reaction mixture was purified on silica gel column to give the titled compound (10-a) [yield:24.4 g(58%)].

3-2) (1S,5R,6R,7R)-6-(4,4-difluoro-3-oxooctyl)-7-tetrahydropyranyloxy)-2-oxabicyclo [3,3,0]octane-3-one (11-a)

The compound (10-a) (12.7 g) in ethyl acetate (300 ml) was catalytically reduced with catalytic amount of 5% Pd—C and hydrogen gas to give the titled compound (11-a) [yield:12.5 g(99%)].

3-3) (1S,5R,6R,7R)-6-[4,4-difluoro-3(R,S) hydroxyoctyl]-7-tetrahydropyranyloxy)-2-oxabicyclo[3,3,0]octane-3-one (12-a)

The compound (11-a) (12.6 g) in methanol (400 ml) was reduced with sodium borohydride (1.25 g) at 0° C. to obtain the titled compound (12-a) [yield:12.1 g(95.5%)].

3-4) [1S,3(R,S)5R,6R,7R)-6-[4,4-difluoro-3(R,S)-hydroxyoctyl]7-(tetrahydropyranyloxy)-2-oxabicyclo[3,3,0]octane-3-ol (13-a)

The compound (12-a) (12.1 g) in toluene (500 ml) was reduced with diisobutyl aluminum hydride (1.5M;65.1 ml) at −78° C., and the product was purified on silica gel column to give the titled compound (13-a) [yield:11.1 g(91%)].

3-5)phenacyl (Z)-9-{(1S,2R,3R,5S)-2-[4,4-difluoro-3(RS)-hydroxyoctyl]-5-hydroxy-3-tetrahydropyranyloxy) cyclopentyl}-7-nonenoate (15-a)

DMSO (40 ml) was added to sodium hydride (60%;1.63 g) which was washed with pentane, and the mixture was maintained at 65–700° C. for 1.5 hours and cooled to room temperature. (6-Carboxyhexyl)triphenylphosphonium bromide (e) (9.61 g) was added to the mixture to form ylide. The solution of the compound (13-a) (2.00 g) in DMSO (15 ml) was dropped to the ylide, and the mixture was held overnight at room temperature. The compound (14-a) was obtained by the conventional treatment of the product [yield:3.18 g(crude product)].

The compound (14-a) (0.795 g), phenacyl bromide (1.01 g) and diisopropylethylamine (0.89 ml) were dissolved in acetonitrile (10 ml), and the solution was maintained at room temperature for 20 minutes and at 45° C. for 30 minutes. The crude product obtained by the conventional treatment of the reaction mixture was purified on silica gel column to give the titled compound (15-a) [yield:0.604 g].

3-6)phenacyl (Z)-9-{(1S,2R,3R)-2-(4,4-difluoro-3-oxooctyl)-5-oxo-3-(tetrahydropyranyloxy)cyclopentyl]-7-nonenoate (16-a)

DMSO (0.92 ml) was dropped to the solution of oxalyl chloride (0.52 ml) in dichloromethane (30 ml) which was cooled to −78° C. The solution of the compound (15-a) (0.609 g) in dichloromethane (15 ml) was added to the mixture, and the resultant mixture was agitated at −30° C.−−20°0 C. for 1.5 hours. Triethylamine (1.88 ml) was added to said mixture, and the resultant mixture was agitated for 30 minutes. The crude product obtained by the conventional treatment of the reaction mixture was purified on silica gel column to give the titled compound (16-a) [yield:0.514 g(85%)].

3-7)phenacyl (Z)-9-[(1R,2R,3R)-2-(4,4-difluoro-3-oxooctyl)-3-hydroxy-5-oxocyclopentyl]-7-nonenoate (16-b)

The compound (16-a)(0.514 g) was dissolved in the solvent mixture (acetic acid:water:THF=4:2:1)(30 ml), and the solution was maintained overnight at room temperature. The titled compound (16-b) was obtained by purifying the crude product on silica gel column [yield:0.272 g(61%)].

Compound (16-b)[compound (6) wherein X$_1$=X$_2$=F, R$_2$–R$_3$=butyl, P$_3$=phenacyl]

NMR(CDCl$_3$) δ: 92(t, 3H, J=7.5 Hz), 1.2–2.9(m, 27H), 4.18(m, 1H), 5.4 (m, 2H), 7.4–8.0 (m, 5H)

3-8) (Z)-9-[(1R,2R,3R)-2-(4,4-difluoro-3-oxooctyl)-3-hydroxy-5-oxocyclopentyl]-7-nonenoic acid (17-a)

The compound (16-b)(0.272 g) was dissolved in acetic acid (10 ml). Zinc (3.5 g) was added little by little at room temperature, and the mixture was agitated for 2.5 hours. The crude product obtained by the conventional treatment of the reaction mixture was purified on silica gel column to give the titled compound (17-a) [yield:0.177 g(81%)].

Compound (17-a)[compound (17) wherein X$_1$=X$_2$=F, R$_2$–R$_3$=butyl]

NMR(CDCl$_3$) δ: 0.93(t, 3H, J=6.5 Hz), 1.15~2.95(m, 28H), 4.19(1H), 5.36(m, 1H)

Synthesis Example 4

Preparation of 2-decarboxy-2-(2-carboxyethyl)-13,14-dihydro-15-keto-16,16-difluoro-PGE$_1$ isopropyl ester [IUPAC name:isopropyl 9-[(1R,2R,3R)-2-(4,4-difluoro-3-oxooctyl)-3-hydroxy-5-oxocyclopentyl]-nonanoate(20-a)

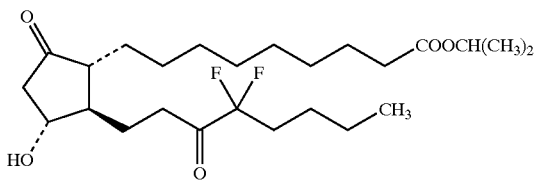

(20-a)

4-1)isopropyl (Z)-9-{(1R,2R,3R,5S)-2-[4,4-difluoro-(3RS)-hydroxyoctyl]-5-hydroxy-3-(tetrahydropyranyloxy) cyclopentyl}-7-nonenoate (15-b)

The compound (14-a) prepared in synthesis example 3 (0.802 g), DBU(0.76 ml) and isopropyl iodide (0.51 ml)

were dissolved in acetonitrile (15 ml), and the solution was maintained at 50° C. for 1 hour. The compound (14-a) (0.492 g) was further reacted in similar manner to give the titled compound (15-b) (yield:0.315 g(total)].

4-2)isopropyl 9-{(1R,2R,3R)-2-[4,4-difluoro-(3RS)-hydroxyoctyl]-5-hydroxy-3-(tetrahydropyranyloxy)cyclopentyl}-nonanoate (18-a)

The compound (15-b) (0.315 g) in ethanol (20 ml) was catalytically reduced with 5% Pd—C (0.08 g) and hydrogen gas to give the titled compound (18-a) [yield:0.301 g(95%)].

4-3)isopropyl 9-[(1R,2R,3R)-2-(4,4-difluoro-3-oxooctyl)-5-oxo-3-(tetrahydropyranyloxy)cyclopentyl]-nonanoate (19-a)

The compound (18-a)(0.301 g) in dichloromethane was subjected to Swan oxidation with oxalyl chloride (0.34 ml), DMSO (0.61 ml) and triethylamine (1.22 ml) to give the titled compound (19-a)[yield:0.288 g(96%)].

4-4)isopropyl 9-[(1R,2R,3R)-2-(4,4-difluoro-3-oxooctyl)-3-hydroxy-5-oxocyclopentyl]nonanoate (20-a)

The compound (19-a)(0.288 g) was dissolved in the solvent mixture (acetic acid:water:THF=4:2:1)(30 ml), and the solution was maintained at 45° C. for 3.5 hours. The crude product obtained by the conventional treatment of the reaction mixture was purified on silica gel column to give the titled compound (20-a) [yield:0.184 g(76%)].

Compound (20-a) [compound (20) wherein $X_1=X_2=F$, $R_2–R_3$=butyl, $P_3$=isopropyl]

NMR(CDCl$_3$) δ: 0.94(t, 3H, J=6.5 Hz), 1.24(d, 6H, J=6 Hz), 1.27~2.95(m, 31H), 4.19(m, 1H), 5.02(Hept, 1H, J=6 Hz)

The compound (I) wherein Y is —CO—CH$_2$— or —C≡C— can be prepared by the following manner.

Synthesis Example 5

Preparation of 2-decarboxy-2-(2-carboxyethyl)-13,14-dihydro-6,15-diketo-PGF$_1$α isopropyl ester (22-a)

(22-a)

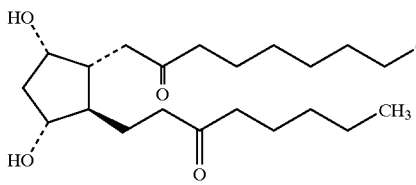

The compound (3-a) prepared in synthesis example 1 was dissolved in the mixture of tetrahydrofuran and methylene chloride, and a small excess amount of N-bromosuccinimide was added and agitated at 0° C. for 5 minutes. The crude product obtained-by the conventional post-treatment of the reaction mixture was purified by column chromatography to obtain the compound (21-a) [compound (21) wherein $X_1=X_2=H$, $R_2–R_3$=butyl, $P_1$=tetrahydropyranyl, $P_2$=ethylene, $P_3$=isopropyl]. Said compound was dissolved in toluene, and DBU was added to the solution. The mixture was agitated overnight at 40° C. The reaction mixture was cooled with ice, acidified with 1N-HCl, agitated for 10 minutes and then extracted with ethyl acetate, The compound (22-b) [(compound (22) wherein $X_1$ and the like have the same meanings as defined above] was obtained by purifying the crude product by means of column chromatography, said crude product being obtained by the conventional post-treatment of the reaction mixture. Said compound was subjected to the same deprotection treatment as in the process of 1-3) in the synthesis example 1 to give the titled compound (22-a).

Synthesis Example 6

Preparation of 2-decarboxy-2-(2-carboxyethyl)-5,6-dehydro-13,14-dihydro-15-keto-PGE$_2$ methyl ester (24-a)

(24-a)

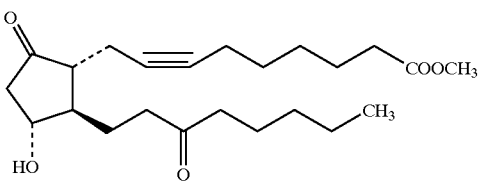

Tertiary butyllithium was dropped to the solution of 8-methoxy-3,3-ethylenedioxy-1-iodooctane (cf. Japanese Patent Publication (KOKAI) No. 52753/1989) in ether over 30 minutes, and the mixture was agitated for 3 hours. The solution of tributyl phosphine and cuprous iodide in ether which was cooled to −78° C. was added at once to the reaction mixture. The resultant mixture was agitated for 20 minutes to produce the complex (a). The solution of 4R-tertiary butyldimethylsilyloxy-2-cyclopentene-1-one (23-a) in tetrahydrofuran was dropped to the reaction mixture over 95 minutes, and the resultant mixture was agitated for 15 minutes and then cooled with the cooling bath (−30° C.). The solution of 8-methoxycarbonyl-1-iodooctane (b) in HMPA was added to said cooled mixture, and the resultant mixture was agitated for 4.5 hours and then agitated at room temperature for 12 hours. The reaction mixture was poured into the aqueous saturated solution of ammonium chloride, and the resultant organic layer was separated. The crude product obtained by the conventional post-treatment of the organic layer was purified by chromatography to give the compound (24-b) [compound (24) wherein $X_1=X_2=H$, $R_2–R_3$=butyl, $P_3$=methyl, $P_5$=tertiary butyldimethylsilyl]. Said compound was deprotected by the ordinary manner to give the titled compound (24-a).

Synthesis Example 7

Preparation of 2-decarboxy-2-(2-carboxyethyl)-13,14-dihydro-15-keto-16,16-difluoro-PGF$_2$α methyl ester [IUPAC name:methyl (Z)-9-[(1R,2R,3R,5S)-2-(4,4-difluoro-3-oxooctyl)-3,5-dihydroxycyclopentyl]-7-nonenoate (32-a)

(32-a)

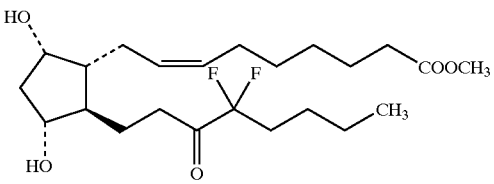

7-1) [1S,3(R,S),5R,6R,7R]-6-[3(R,S)-t-butyldimethylsilyloxy-4,4-difluorooctyl]-7-tetrahydropyranyloxy-2-oxabicyclo[3.3.0]octane-3-ol (26-a)

The compound (12-a) [compound (12) wherein $X_1=X_2=F$, $P_1$=tetrahydropyranyl, $R_2–R_3$=butyl](1.26 g) in DMF (15 ml) was converted into silylether (25-a) with imidazole (2.63 g) and t-butyldimethylsilane chloride (2.91 g)[yield:1.43 g(88%)]. The silyl ether (25-a) (1.43 g) was reduced with diisobutyl aluminium hydride by the ordinary manner to give the titled compound (26-a) [yield:1.47 g(100%)].

7-2) methyl (Z)-9-{(1R,2R,3R,5S)-2-[3(R,S)-t-butyldimethylsilyloxy-4,4-difluorooctyl]-5-hydroxy-3-tetrahydropyranyloxy)cyclopentyl}-7-nonenoate (28-a)

The ylide was prepared with sodium hydride (60%;0.934 g), DMSO (25 ml) and (6-carboxyhexyl) triphenylphosphonium bromide (5.50 g) by the ordinary manner. The solution of the compound (26-a) in ether (8 ml) was added to the reaction mixture, and the resultant mixture was agitated at room temperature for 2 hours. The carboxylic acid (27-a) obtained by the conventional treatment of the reaction mixture was treated with diazomethane, and the treated product was purified on silica gel column to give the titled compound (28-a) [yield;0.43 g(48%)].

7-3) methyl (Z)-9-{(1R,2R,3R,5S)-2-[3(R,S)-t-butyldimethylsilyloxy-4,4-difluorooctyl]-3,5-ditetrahydropyranyloxy)cyclopentyl}-7-nonenoate (29-a)

The compound (28-a) (0.438 g) in dichloromethane (25 ml) was converted into ditetrahydropyranyl ether with an excess amount of dihydropyran and a catalytic amount of p-toluenesulfonic acid. Said product was purified on silica gel column to obtain the titled compound (29-a) [yield:0.494 g(99%)].

7-4)(Z)-9-[(1R,2R,3R,5S)-2-oxy-4,4-difluoro-3-oxooctyl)-3,5-ditetrahydropyranyloxy)cyclopentyl]-7-methyl nonenoate (31-a)

The compound (29-a) (0.494 g) was dissolved in THF (10 ml), and tetrabutylammonium fluoride (1.0 M;5.6 ml) was added to the solution. The mixture was left overnight at room temperature. The crude product obtained by the conventional treatment of the reaction mixture was purified on silica gel column to give the deprotected compound (30-a) [yield:0.284 g(68%)].

The compound (30-a) (0.284 g) in dichloromethane (10 ml) was subjected to Swan oxidation with oxalyl chloride (0.165 ml) and DMSO (0.3 ml). The titled compound (31-a) was obtained by purifying the crude product on silica gel column [yield:0.251 g(89%)].

7-5) methyl (Z)-9-[(1R,2R,3R,5S)-2-(4,4-difluoro-3-oxooctyl)-3,5-dihydroxycyclopentyl]-7-nonenoate (32-a)

The compound (31-a)(0.251 g) was dissolved in the solvent mixture (acetic acid:water:THF=4:2:1)(30 ml), and the solution was maintained at 45–50° C. for 3 hours. The crude product obtained by the conventional treatment of the reaction mixture was purified on silica gel column to give the titled compound (32-a) [yield:0.137 g(76%)].

The compound (32-a) [compound (32) wherein $X_1=X_2=F$, $R_2-R_3$=butyl, $P_3$=methyl]

NMR(CDCl$_3$) δ: 0.92(t,3H, J=7.5 Hz), 1.2–2.9(m, 38H), 3.67(s, 3H), 3.70 (q, 1H, J=7.5 Hz), 4.25 (m, 1H), 5.43 (m, 2H)

Synthesis Example 8

Preparation of 2-decarboxy-2-(2-carboxyethyl)-13,14-dihydro-15-keto-16,16-difluoro-PGE$_1$ [IUPAC name:9-[(1R,2R,3R,5S)-2-(4,4-difluoro-3-oxooctyl)-3-hydroxy-5-oxocyclopentyl]nonanoic acid (33-a)

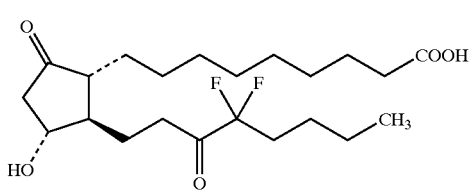

(33-a)

8-1) benzyl (Z)-9-{(1S,2R,3R,5S)-2-[4,4-difluoro-3(R,S)-hydroxyoctyl]-5-hydroxy-3-(tetrahydropyranyloxy)cyclopentyl}-7-nonenoate (15-c)

The compound (14-b) [compound (14) wherein $X_1=X_2=F$, $P_1$=tetrahydropyranyl, $R_2-R_3$=butyl] (1.09 g) was dissolved in acetonitreile (20 ml). DBU (2.6 ml) and benzyl bromide (2.2 ml) were added to the solution, and the resultant mixture was maintained at 45° C. for 1 hour and at 60° C. overnight. The crude product obtained by the conventional treatment of the reaction mixture was purified on silica gel column to give the titled compound (15-c) (yield:0.213 g).

8-2) benzyl (Z)-9-[(1R,2R,3R,5S)-2-(4,4-difluoro-3-oxooctyl)-3-tetrahydropyranyloxy)-5-oxocyclopentyl]-7-nonenoate (16-c)

The compound (15-c) (0.213 g) in dichloromethane (15 ml) was subjected to Swan oxidation with oxalyl chloride (0.23 ml), DMSO (0.41 ml) and triethylamine (0.81 ml). The titled compound (16-c) was obtained by purifying the crude product on silica gel column (yield:0.181 g(86%)].

8-3) benzyl (Z)-9-[(1R,2R,3R,5S)-2-(4,4-difluoro-3-oxooctyl) -3-hydroxy-5-oxocyclopentyl)-7-nonenoate (6-c)

The compound (16-c)(0.181 g) was dissolved in the solvent mixture [acetic acid:water:THF=(4:2:1)](25 ml), and the solution was maintained at 45° C. for 3.5 hours. The crude product obtained by the conventional treatment of the reaction mixture was purified on silica gel column to give the titled compound (6-c) [yield:0.140 g(91%)].

The compound (6-c) [compound (6) wherein $X_1=X_2=F$, $R_2-R_3$=butyl, $P_3$=methyl]

NMR(CDCl$_3$) δ: 0.93(t,3H, J=7.5 Hz), 1.2–2.8(m, 27H), 4.20(m, 1H), 5.12 (s, 2H), 5.2–5.5 (m, 2H), 7.35 (m, 5H)

8-4) 9-[(1R,2R,3R,5S)-2-(4,4-difluoro-3-oxooctyl)-3-hydroxy-5-oxocyclopentyl]nonanoic acid (33-a)

The compound (6-c) (0.140 g) was dissolved in ethyl acetate (15 ml), and the solution was subjected to catalytic reduction with Pd-C (50 mg) and hydrogen gas. After filtering off the catalyst, the crude product obtained by concentrating the filtrate was purified with Lobar column (ODS) to obtain the titled compound (33-a) [yield:0.077 g(65%)].

The compound (33-a) [compound (33) wherein $X_1=X_2=F$, $R_2-R_3$=butyl]

NMR(CDCl$_3$) δ: 0.95(t, 3H, J=7.5 Hz), 1.2–2.8(m, 32H), 4.20(m, 1H)

Synthesis Example 9

Preparation of 2-decarboxy-2-(2-carboxyethyl)-13,14-dihydro-15-keto-16,16-difluoro-20-ethyl-PGE$_1$ isopropyl ester [IUPAC name:isopropyl 9-[(1R,2R,3R)-2-(4,4-difluoro-3-oxodecyl)-3-hydroxy-5-oxocyclopentyl]-nonanoate] (20-b)

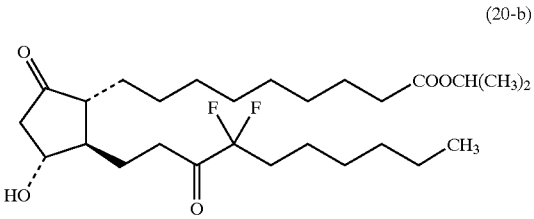

(20-b)

The titled compound (20-b) was obtained by the same manner as in the synthesis example 4 with the exception that dimethyl(3,3-difluoro-2-oxononyl)phosphonate was used as alkylphosphonate.

The compound (20-b) [compound (20) wherein $X_1=X_2=F$, $R_2$–$R_3$=hexyl, $P_3$=isopropyl]

NMR (CDCl$_3$) δ: 0.90 (t, 3H, J=7.5 Hz), 1.32 (d, 6H, 6 Hz), 1.25–2.70 (m, 34H), 3.15 (s, 1H) 4.20 (m, 1H), 5.00 (Hept, 1H, 7.5 Hz)

Synthesis Example 10

Preparation of 2-decarboxy-2-(2-carboxyethyl)-13,14-dihydro-15-keto-PGE$_2$ isopropyl ester [IUPAC name:isopropyl (Z)-9-[(1R,2R,3R)-2-(3-oxooctyl)-3-hydroxy-5-oxocyclopentyl]-nonanoate] (6-d)

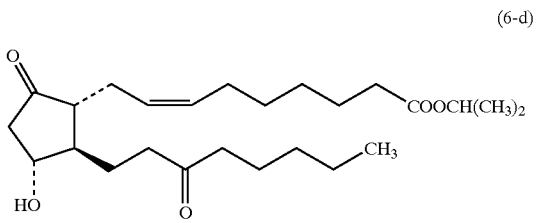

(6-d)

The titled compound (6-d) was obtained by the same manner as in the synthesis example 2 with the exception that dimethyl (2-oxoheptyl) phosphonate was used as alkylphosphonate.

The compound (6-d) [compound (6) wherein $X_1=X_2=H$, $R_2$–$R_3$=butyl, $P_3$=isopropyl]

NMR (CDCl$_3$) δ: 0.89 (t, 3H, J=6.6 Hz), 1.18 (d, 6H, 6.2 Hz), 1.15–3.0 (m, 29H), 4.04 (m, 1H), 4.99 (Hept, 1H, 6.2 Hz), 5.37 (m, 2H)

Synthesis Example 11

Preparation of isopropyl 9[2(R)-4,4-difluoro-3oxodece-1-nyl)-3(R)-hydroxy-5-oxocyclopentyl]nonanoate (11-14);[2-decarboxy-2-(2-carboxyethyl)-15-keto-16,16-difluoro-20-ethyl-PGE$_1$ isopropyl ester (11-14)

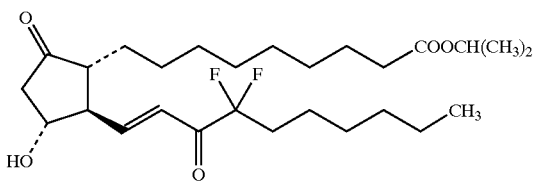

(11-14)

[1S,3(RS),5R,6R,7R]-6-(t-butyldimethylsiloxymethyl)-7-(tetrahydropyranyloxy)-2-oxabicyclo[3.3.0]octa-3-ol (11-2)

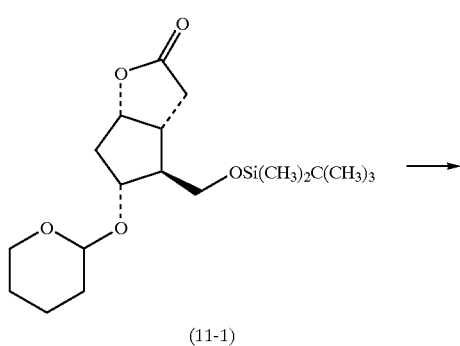

(11-1)

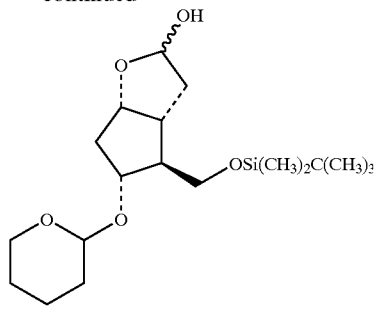

(11-2)

(1S,5R,6R,7R)-(t-Butyldimethylsiloxymethyl)-7-(tetrahydropyranyloxy)-2-oxabicyclo(3.3.0]octa-3-one (11-1) (2.97 g) in toluene was reduced with DIBAL-H (1.6M;1.2 ml) at −78° C. The titled compound (11-2) was obtained by the conventional treatment of the reaction product [yield:2.81 g(95%)].

11-2)
7(Z)-9-[2(R)-(t-Butyldimethylsiloxymethyl)-5(R)-hydroxy-3(R)-(tetrahydropyranyloxy)cyclopentyl]non-7-enoic acid (11-3)

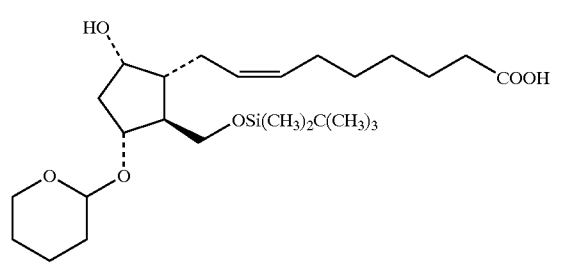

(11-3)

The solution of lactol (11-2) (2.81 g) in THF(10 ml) was added to the ylide prepared from the reaction of (6-carboxyhexyl) triphenylphosphonium bromide (10.7 g) in THF (28 ml) with potassium t-butoxide (1M solution in THF;45.2 ml), and the mixture was agitated overnight at room temperature. The titled compound (11-3) was obtained by the conventional treatment of the reaction product (yield:6.90 g).

11-3)
Isopropyl 7(Z)-9-[2(R)-(t-butyldimethylsiloxymethyl)-5(R)-hydroxy-3(R)-(tetrahydropyranyloxy)cyclopentyl]non-7-enoate (11-4)

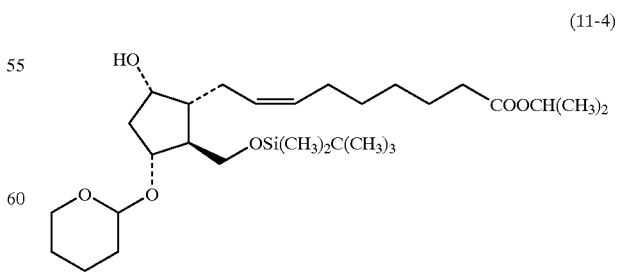

(11-4)

Carboxylic acid (11-3) (6.90 g) in acetonitrile (35 ml) was converted into isopropyl ester with isopropyl iodide (2.25 ml) and DBU (3.38 ml). The crude product obtained by the conventional treatment of the reaction mixture was purified by silica gel chromatography (n-hexane/ethyl acetate=5/1–3/1) to obtain the titled isopropyl ester (11.4) [yield:3.29 g(77%; 3 reaction processes)].

11-4)

Isopropyl 7(Z)-9-[S(R)-(acetoxy)-2(R)-(t-butyldimethylsiloxymethyl)-3(R)-(tetrahydropyranyloxy)cyclopentyl]non-7-enoate (11-5)

(11-5)

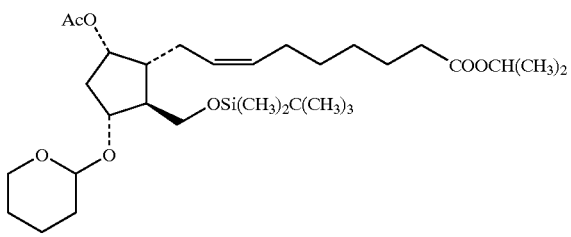

The compound (11-4) (3.29 g) in dichloromethane was acetylized with dimethylaminopyridine (1.84 g) and acetic anhydride (1.84 g). The titled compound (11-5) was obtained by the conventional treatment of the reaction mixture (yield:3.79 g).

11-5)

Isopropyl 7(Z)-9-[5(R)-(acetoxy)-2(R)-hydroxymethyl)-3(R)-(tetrahydropyranyloxy)cyclopentyl]non-7-enoate (11-6)

(11-6)

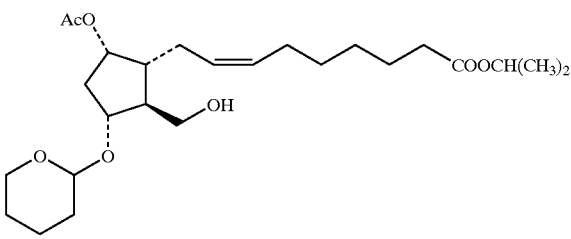

Tetrabutylammonium fluoride [1.0M (THF solution);7.5 ml] was added to the compound (11-5) (3.79 g) in THF (50 ml), and the mixture was agitated overnight at room temperature. The crude product obtained by the conventional treatment of the reaction mixture was purified by silica gel chromatography (n-hexane/ethyl acetate=3/2–2/3) to give the titled compound (11-6) [yield:2.91 g(83%)]. 11-6)

Isopropyl 9-[5(R)-(acetoxy)-2(R)-hydroxymethyl)-3(R)-(tetrahydropyranyloxy)cyclopentyl]nonanoate (11-7)

(11-7)

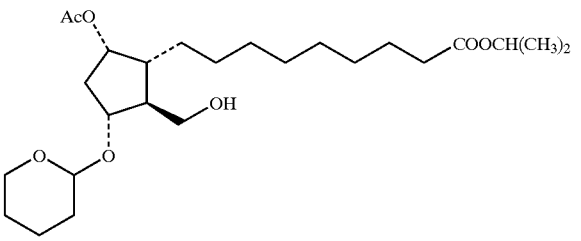

The compound (11-6) (2.84 g) in ethyl acetate (20 ml) was subjected to catalytic reduction with 5% Pd—C (0.284 g) and hydrogen gas at room temperature. The crude product was purified by silica gel chromatography (n-hexane/ethyl acetate=1/1 ethyl acetate) to give the titled compound (11-7) [yield:2.34 g(82%)].

11-7)

Isopropyl 9-[5(R)-(acetoxy)-2(R)-formyl-3(R)-(tetrahydropyranyloxy)cyclopentyl]nonanoate (11-8)

(11-8)

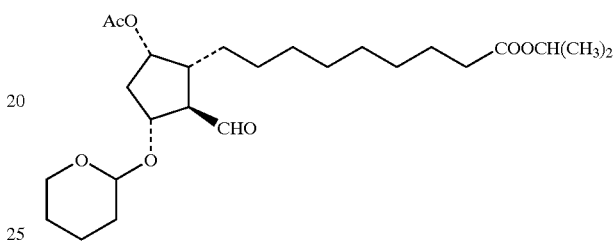

The compound (11-7) (2.34 g) in dichloromethane (−78° C.) was subjected to Swan oxidation with oxalyl chloride [2M($CH_2Cl_2$ solution);1.2 ml], DMSO(0.34 ml) and triethylamine (2.5 ml). The titled compound (11-8) was obtained by the conventional treatment of the reaction mixture.

11-8)

Isopropyl 9-[5(R)-(acetoxy)-2(R)-(4,4-difluoro-3-oxodece-1-nyl)-3(R)-(tetrahydropyranyloxy)cyclopentyl]nonanoate (11-9)

(11-9)

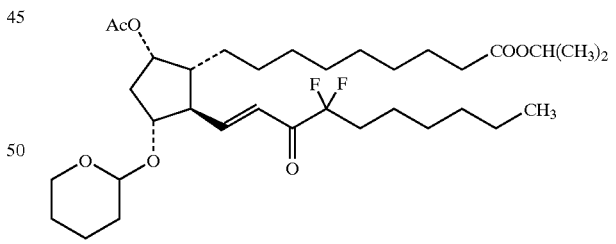

Sodium hydride (60%;0.096 g) was suspended in THF (4 ml) at 0° C., and the solution of dimethyl (3,3-difluoro-2-oxononyl)phosphonate (1.03 g) in THF(4 ml) was added to the suspension. The mixture was agitated for 20 minutes, and the solution of the compound (11-8) in THF (6 ml) was dropped to said mixture. The resultant mixture was refluxed overnight. The crude product obtained by the conventional treatment of the reaction mixture was purified by silica gel chromatography (n-hexane/ethyl acetate=9/1–17/3) to give the titled compound (11-9) [yield:0.51 g(69%)].

11-9)

Isopropyl 9-{5(R)-(acetoxy)-2(R)-[4,4-difluoro-3-(RS)-hydroxydece-1-nyl]-3(R)-(tetrahydropyranyloxy)cyclopentyl}nonanoate (11-10)

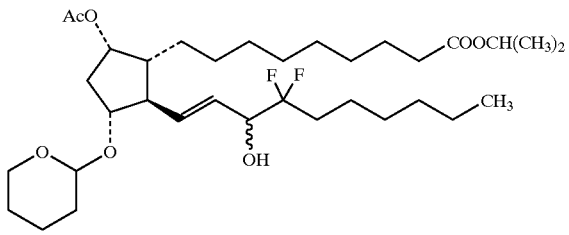

(11-10)

The compound (11-9) (0.51 g) was reduced with zinc borohydride prepared by the reaction of sodium borohydride (0.19 g) and zinc chloride (0.34 g) in ether (8 ml). The crude product obtained by the conventional treatment of the reaction mixture was purified by silica gel chromatography (n-hexane/ethyl acetate=4/1–3/1) to give the titled compound (11-10) [yield:0.47 g(93%)].

11-10)

9-{5(R)-[4,4-difluoro-3-(RS)-hydroxydece-1-nyl]-5(R)-hydroxy-3(R)-tetrahydropyranyloxy)cyclopentyl}nonanoic acid (11-11)

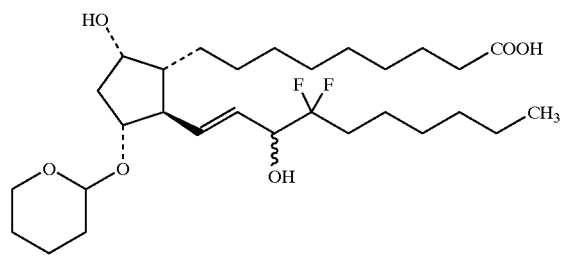

(11-11)

The compound (11-10) (0.47 g) was dissolved in ethanol (8 ml), and 1N sodium hydroxide solution (7.7 ml) was added to the solution. The mixture was agitated overnight at room temperature. The titled compound (11-11) was obtained by the conventional treatment of the reaction mixture.

11-11)

Isopropyl 9-{2(R)-[4,4-difluoro-3(RS)-hydroxydece-1-nyl]-5(R)-hydroxy-3(R)-(tetrahydropyranyloxy)cyclopentyl}nonanoate (11-12)

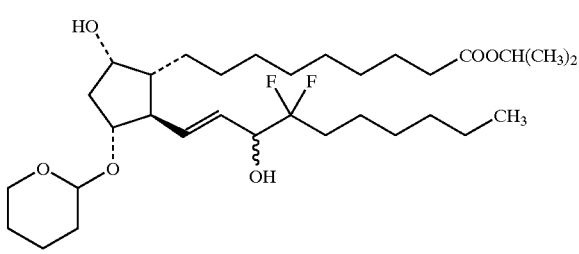

(11-12)

The compound (11-11) in acetonitrile (6 ml) was converted into isopropyl ester with DBU (0.35 ml) and isopropyl iodide (0.23 ml) at 50° C. The crude product obtained by the conventional treatment of the reaction mixture was purified by silica gel chromatography (n-hexane/ethyl acetate=65/35–55/45) to give the titled compound (11-12) [yield:0.34 g(76%;2 reaction processes)].

11-12)

Isopropyl 9-[2(R)-(4,4-difluoro-3-oxodece-1-nyl]-5-oxo-3(R)-(tetrahydropyranyloxy)cyclopentyl]nonanoate (11-13)

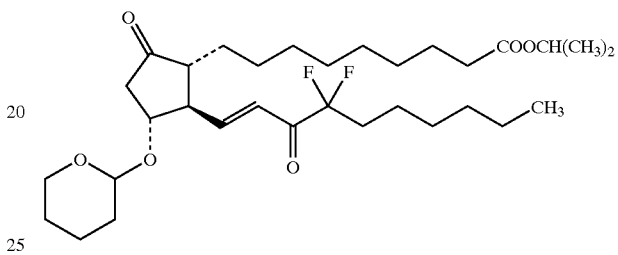

(11-13)

The compound (11-12) (0.34 g) in dichloromethane (8 ml) was subjected to Swan oxidation at −78° C. with oxalyl chloride [2M(CH$_2$Cl$_2$ solution);1.47 ml], DMSO (0.42 ml) and triethylamine (3.3 ml). The crude product was purified by silica gel chromatography (n-hexane/ethyl acetate=85/15–75/25) to give the titled compound (11-13) [yield:0.24 g(71%)].

11-13)

Isopropyl 9-[2(R)-(4,4-difluoro-3-oxodece-1-nyl]-3(R)-hydroxy-5-oxocyclopentyl]nonanoate (11-14)

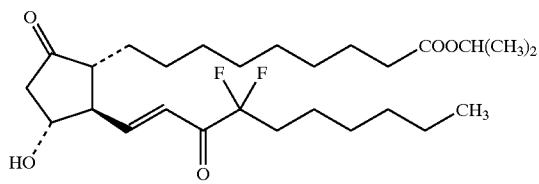

(11-14)

The compound (11-13) (0.24 g) was dissolved in the solvent mixture [acetic acid:water:THF(4:2:1)] (10 ml), and the solution was maintained at 40° C. for 3.5 hours. The crude product obtained by the conventional treatment of the reaction mixture was purified by silica gel chromatography (n-hexane/ethyl acetate=7/3) to give the titled compound (11-14) [yield:0.17 g(82%)].

Compound (11-14)

N.m.r.(CDCl$_3$) δ: 0.89(3H,t,J=7.1 Hz), 1.21(6 H,d,J=6.5 Hz), 1.22–2.90(31H,m), 4.27(1H,q, J=7.6 Hz), 5.00(1H, sept,J=6.5 Hz), 6.73(1H, d,J=15 Hz), 7.12(1H,dd,J=15 Hz,J=8.6 Hz) Mass. m/z 422(M$^+$), 404(M$^+$-H$_2$O)

Synthesis Example 12

Preparation of isopropyl 9-{2(R)-[4,4-difluoro-3(R)-hydroxydecyl]-3(R)-(hydroxy-5-oxocyclopentyl}nonanoate (12-12);[2-decarboxy-2-(2-carboxyethyl)-13,14-dihydro-16,16-difluoro-20-ethyl-PGE$_1$ isopropyl ester (12-12)

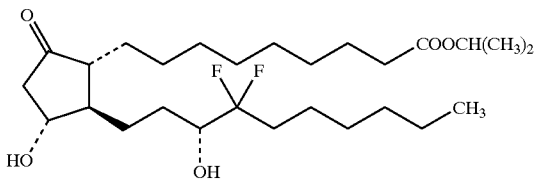

(12-12)

12-1)
(1S,5R,6R,7R)-6-(4,4-difluoro-3-oxodece-1-nyl)-7-(tetrahydropyranyloxy)-2-oxabicyclo[3.3.0]octan-3-one (12-3)

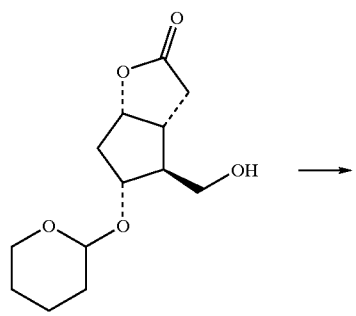

(12-1)

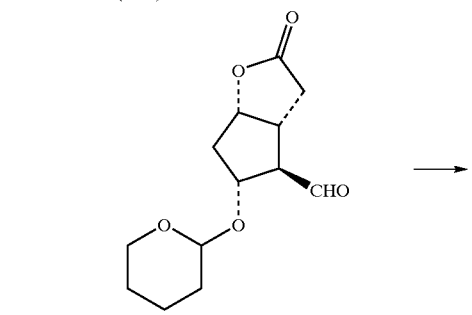

(12-2)

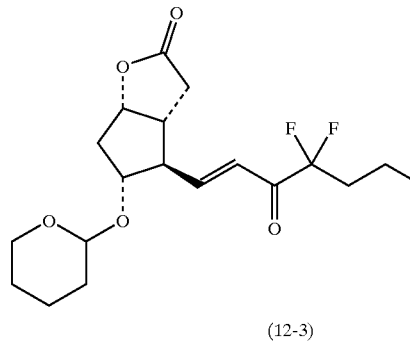

(12-3)

Corey lactone (12-1) (7.10 g) in dichloromethane (200 ml) was subjected to Swan oxidation at −78° C. with oxalyl chloride [2.0M(CH$_2$Cl$_2$ solution);30 ml], DMSO (8.45 ml) and triethylamine (16.9 ml). By the conventional treatment of the reaction mixture, (1S,5R,6R,7R)-6-formyl-7-(4,4-difluoro-3-oxodece-1-nyl)-7-(tetrahydropyranyloxy)-2-oxabicyclo[3.3.0]octane-3-one (12-2) (Corey aldehyde (12-2)) was obtained. The solution of dimethyl(3,3-difluoro-2-oxononyl)phosphonate (7.93 g) in THF (10 ml) was added to the suspension of sodium hydride (60%;1.11 g) in THF (10 ml), and the mixture was agitated for 15 minutes, and then zinc chloride (3.77 g) was added to the mixture. After adding the solution of Corey aldehyde (12-2) in THF (15 ml), the resultant mixture was agitated. The crude product obtained by the conventional treatment of the reaction mixture was purified by silica gel chromatography (n-hexane/ethyl acetate=65/35) to obtain the titled compound (12-3) [yield:5.75 g(50%)].

12-2)
(1S,5R,6R,7R)-6-[4,4-difluoro-3(RS)-hydroxydece-1-nyl]-7-(tetrahydropyranyloxy)-2-oxabicyclo[3.3.0]octa-3-one (12-4)

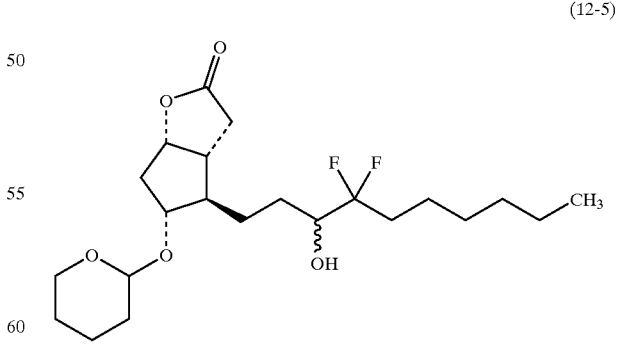

The solution of the compound (12-3) (4.15 g) in THF (30 ml) was added to zinc borohydride prepared by the reaction of sodium borohydride (3.03 g) and zinc chloride (5.45 g) in ether (20 ml) to reduce said compound. The crude product obtained by the conventional treatment of the reaction mixture was purified by silica gel chromatography (n-hexane/ethyl acetate=50/50) to give the titled compound (12-4) [yield:3.88 g(93%)].

12-3)
(1S,5R,6R,7R)-6-[4,4-difluoro-3(RS)-hydroxydecyl]-7-(tetrahydropyranyloxy)-2-oxabicyclo[3.3.0]octa-3-one (12-5)

The compound (12-4) (2.50 g) in ethyl acetate (30 ml) was subjected to catalytic reduction with 5% Pd—C (0.25 g) under H$_2$ atmosphere. The product was purified by silica gel chromatography (n-hexane/ethyl acetate=1/1) to give the titled compound (12-5) [yield:2.16 g(86%)].

12-4)

(1S,5R,6R,7R)-6-[3(RS)-(t-butyldimethylsiloxy)-4,4-difluorodecyl]-7-(tetrahydropyranyloxy)-2-oxabicyclo[3.3.0]octa-3-one (12-6)

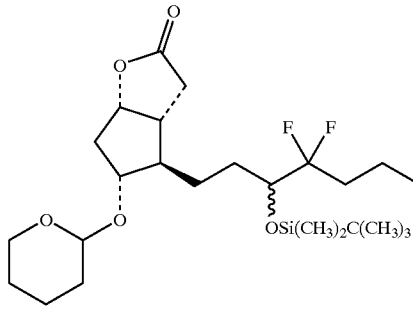

(12-6)

The compound (12-5) (0.76 g) in DMF (4 ml) was agitated at 50° C. for 15 hours in the presence of imidazole (0.31 g) and t-butyldimethylsilane chloride (0.33 g). The crude product obtained by the coventional treatment of the reaction mixture was purified by silica gel chromatography (n-hexane/ethyl acetate=7/3) to give the titled compound (12-6) [yield:0.81 g(83%)].

The compound (12-6) was obtained by the same manner as described above by treating the compound (12-5) (1.05 g) in DMF (7 ml) with imidazole (0.43 g) and t-butyldimethylsilane chloride (0.45 g) [yield:1.07 g(80%)].

12-5)

[1S,3(RS),5R,6R,7R]-6-[3(RS)-(t-butyldimethylsiloxy)-4,4-difluorodecyl]-7-(tetrahydropyranyloxy)-2-oxabicyclo[3.3.0]octa-3-ol (12-7)

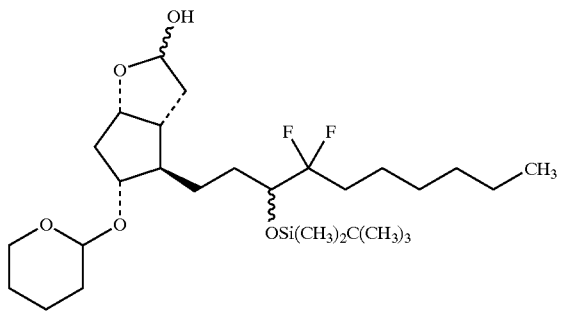

(12-7)

The compound (12-6) (1.46 g) in toluene (7 ml) was reduced at −78° C. with diisobutylaluminium hydride (DIBAL-H) [1.0M (toluene solution);8.2 ml]. The lactol (12-7) was obtained by the conventional treatment of the reaction mixture (yield:1.47 g(100%)].

12-6)

Isopropyl 9(Z)-{2(R)-[3(RS)-(t-butyldimethylsiloxy)-4,4-difluorodecyl]-5(R)-hydroxy-3(R)-(tetrahydropyranyloxy)cyclopentyl}non-7-enoate (12-9)

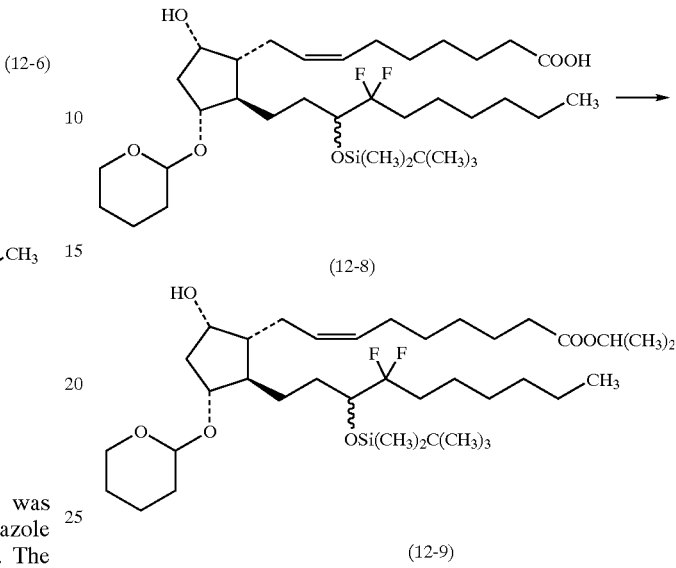

(12-8)

(12-9)

Potassium t-butoxide [1.0M(THF solution);16.4 ml) was added to the suspension of (6-carboxyhexyl)triphenylphosphonium bromide (3.87 g) in THF (7 ml), and the mixture was agitated for 30 minutes at room temperature. After cooling to −15° C., the solution of lactol (12-7) (1.47 g) in THF (7 ml) was added to the mixture, and the resultant mixture was warmed slowly to room temperature and left overnight. By the conventional treatment of the reaction mixture, 9(Z)-{2(R)-[3(RS)-(t-butyldimethylsiloxy)-4,4-difluorodecyl]-5(R)-hydroxy-3(R)-tetrahydropyranyloxy)cyclopentyl}non-7-enoic acid (12-8) was obtained (yield:3.15 g).

The crude carboxylic acid (12-8) was dissolved in acetonitrile (10 ml), and isopropyl iodide (1.09 ml) and DBU (1.63 ml) were added to the solution. The mixture was held overnight at 40° C. The crude product obtained by the conventional treatment of the reaction mixture was purified by silica gel chromatography (n-hexane/ethyl acetate=8/2) to give the titled compound (12-9) [yield:1.39 g (74%;3 reaction processes)).

12-7)

Isopropyl 9-{2(R)-[3(RS)-(t-butyldimethylsiloxy)-4,4-difluorodecyl]-5(R)-hydroxy-3(R)-(tetrahydropyranyloxy)cyclopentyl}nonanoate (12-10)

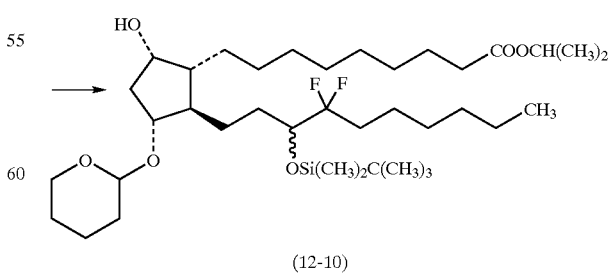

(12-10)

The compound (12-9)(1.39 g) was subjected to catalytic reduction in ethyl acetate (15 ml) using 5% Pd—C (0.14 g)

under hydrogen atmosphere. The crude product obtained by the conventional treatment was purified by silica gel chromatography (n-hexane/ethyl acetate=8/2) to give the titled compound (12-10).

Yield:1.09 g(78%)

12-8)

Isopropyl 9-{2(R)-[3(RS)-(t-butyldimethylsiloxy)-4,4-difluorodecyl]-5-oxo-3(R)-(tetrahydropyranyloxy)cyclopentyl}nonanoate (12-11)

(12-11)

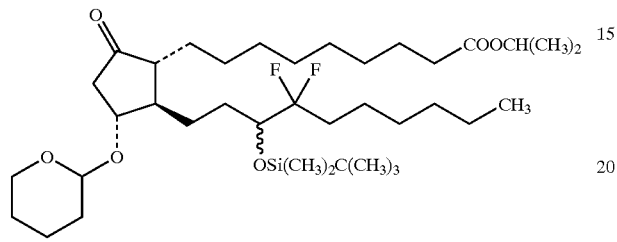

A solution of the compound (12-10)(1.09 g) in dichloromethane (2 ml) was subjected to Swan oxydation using oxalyl chloride(2.0M, $CH_2Cl_2$ solution, 1.58 ml), a solution of DMSO (0.45 ml) in dichloromethane (10 ml) and triethylamine (0.88 ml). The crude product obtained by the conventional treatment was purified by silica gel chromatography (n-hexane/ethyl acetate=8/2) to give the titled compound (12-11).

Yield:0.93 g(86%)

12-9)

Isopropyl 9-{2(R)-[4,4-difluoro-3(R)-hydroxydecyl]-3(R)-hydroxy-5-oxocyclopentyl}nonanoate (12-12)

(12-12)

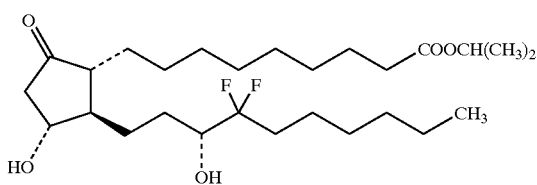

The compound (12-11)(0.93 g) was hydrolyzed in acetonitrile (30 ml) with 46% hydrofluoric acid(1.55 ml). The crude product obtained by the conventional treatment was purified by silica gel chromatography (n-hexane/ethyl acetate=7/3–1/1), and the compound obtained was further fractionated by HPLC to give isopropyl 9-{2(R)-[4,4-difluoro-3(R)-hydroxydecyl]-3(R)-hydroxy-5-oxocyclopentyl}nonanoate (12-12).

Yield:0.16 g(24%)

N.m.r.($CDCl_3$) δ: 0.89(3H,t,J=7.0 Hz), 1.22(6H,d,J=6.5 Hz), 1.24–2.80(36H,m), 3.73(1H,m), 4.16(1H,q,J=6.5 Hz), 5.00 (1H,Sept,J=6.5 Hz)

Mass. m/z:490($M^+$),472($M^+$-$H_2O$)

Rf.value: 0.50 (silica gel 60, n-hexane/ethyl acetate=3/7);

And 0.15 g of 17β-isomer was obtained.

Synthesis Example 13

Preparation of isopropyl 9-{2(R)-[4,4-difluoro-3(R)-hydroxydece-1-nyl]-3(R)-hydroxy-5-oxocyclopentyl}nonanoate (13-12); [2-decarboxy-2-(2-carboxyethyl)-16,16-difluoro-20-ethyl-$PGE_1$ isopropyl ester] (13-12)

(13-12)

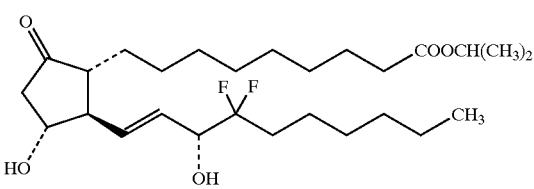

13-1)

Isopropyl 9-[2(R)-(t-butyldimethlysiloxymethyl)-5(R)-hydroxy-(3R)-(tetrahydropyranyloxy)cyclopentyl]nonanoate (13-2)

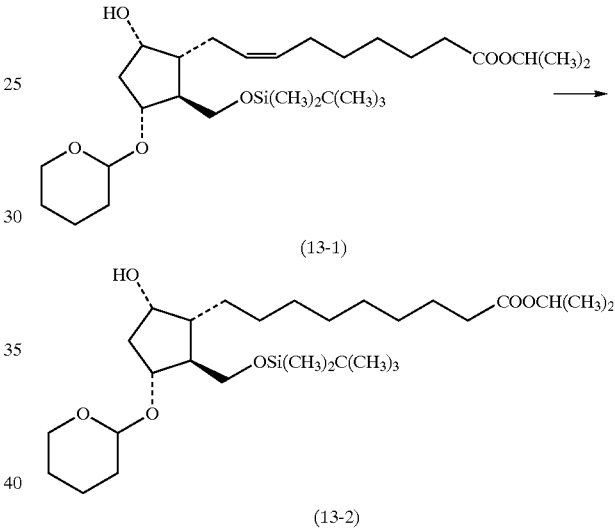

The compound (13-1)(5.89 g) obtained according to the same way as in Experiments (1—1)–(1–3) of Example 1 was subjected to catalytic reduction in ethyl acetate (80 ml) with 5% Pd—C (0.6 g) and hydrogen gas. The crude product obtained by the conventional treatment was purified by silica gel chromatography (n-hexane/ethyl acetate=8/2) to give the titled compound (13-2).

Yield:3.93 g(66%)

13-2)

Isopropyl 9-[5(R)-(acetoxy)-2(R)-(t-butyldimethlysiloxymethyl)-3(R)-(tetrahydropyranyloxy)cyclopentyl]nonanoate (13-3)

(13-3)

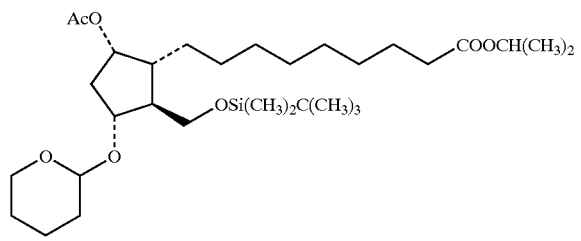

The compound (13-2)(3.93 g) was acetylated in dichloromethane (40 ml) at room temperature using pyridine(1.80 ml) and acetyl chloride (1.59 ml). The titled compound (13-3) was obtained by the conventional treatment.

Yield:4.05g(95%)

13-3)

Isopropyl 9-[5(R)-(acetoxy)-2(R)-(hydroxymethyl)-3(R) - (tetrahydropyranyloxy)cyclopentyl]nonanoate (13-4)

(13-4)

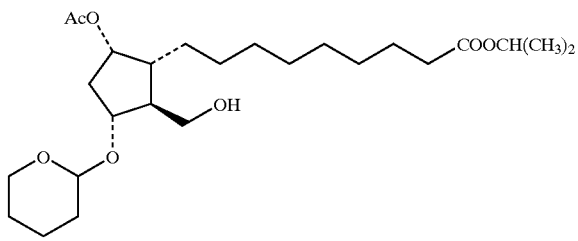

To the solution of the compound (13-3)(4.05 g) in THF(8 ml), tetrabutylammonium fluoride (1M, THF solution, 8.51 ml) was added at room temperature and the mixture was left overnight. The crude product obtained by the conventional treatment was purified by silica gel chromatography (n-hexane/ethyl acetate=6/4) to give the titled compound (13-4).

Yield:3.18 g(98%)

13-4)

Isopropyl 9-[5(R)-(acetoxy)-2(R)-formyl-3(R)-(tetrahydropyranyloxy) cyclopentyl]nonanoate (13-5)

(13-5)

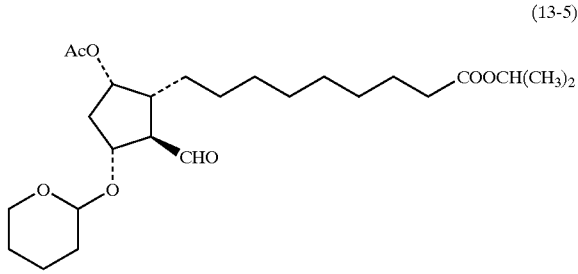

A solution (10 ml) of the compound (13-4)(3.18 g) in dichloromethane was subjected to Swan oxydation using oxalyl chloride(2M, $CH_2Cl_2$ solution, 8.78 ml), a solution (20 ml) of DMSO (2.49 ml) in dichloromethane and triethylamine (5.87 ml). The crude product obtained by the conventional treatment was purified by silica gel chromatography (n-hexane/ethyl acetate=7/3) to give the titled compound (13-5).

Yield:3.10 g(98%)

13-5)

Isopropyl 9-[5(R)-(acetoxy)-2(R)-(4,4-difluoro-3-oxodece-1-nyl)-3(R)-(tetrahydropyranyloxy)cyclopentyl] nonanoate (13-6)

(13-6)

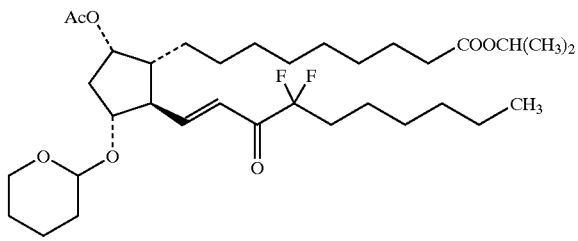

To dimethyl(3,3-difluoro-2-oxononyl)phosphonate anion prepared from sodium hydride (60%, 0.83 g) suspended in THF (20 ml) and dimethyl(3,3-difluoro-2-oxononyl) phosphonate(5.95 g), a solution (20 ml) of the aldehyde (13-5)(3.10 g) in THF was added and refluxed as heating for 70 hours. The crude product obtained by the conventional treatment was purified by silica gel chromatography (n-hexane/ethyl acetate=85/15) to give the titled compound (13-6).

Yield:2.96 g(71%)

13-6)

Isopropyl 9-{5(R)-(acetoxy)-2(R)-[4,4-difluoro-3(RS)-hydroxydece-1-nyl]-3(R)-(tetrahydropyranyloxy) cyclopentyl}nonanoate (13-7)

(13-7)

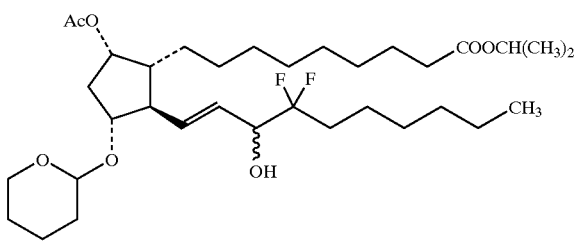

To zinc borohydride prepared from sodium borohydride (1.09 g) and zinc chloride (1.97 g), a solution (10 ml) of α,β-unsaturated ketone (13-6)(2.96 g) in THF was added in ether (40 ml) and the mixture was stirred for 1 hour at 0° C. The crude product obtained by the conventional treatment was purified by silica gel chromatography (n-hexane/ethyl acetate=8/2) to give the titled compound (13-7).

Yield:2.62 g(89%)

13-7)

Isopropyl 9-{5(R)-(acetoxy)-2(R)-[4,4-difluoro-3(RS)-(t-butyldimethylsiloxy)dece-1-nyl]-3(R)-(tetrahydropyranyloxy)cyclopentyl}nonanoate (13-8)

(13-8)

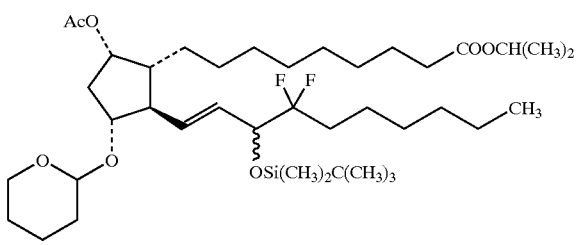

The compound (13-7)(2.62 g) was dissolved in DMF (16 ml) and to resultant solution, imidazol (2.89 g) and t-butyldimethylsilane chloride (3.20 g) were added. The mixture was stirred over three days. The crude product obtained by the conventional treatment was purified by silica gel chromatography (n-hexane/ethyl acetate=85/15) to give the titled compound (13-8).

Yield:3.11 g(100%) 13-8)

Isopropyl 9-{5(R)-[4,4-difluoro-3(RS)-(t-butyldimethylsiloxy)dece-1-nyl]-3(R)-(tetrahydropyranyloxy)cyclopentyl}nonanoate (13-10)

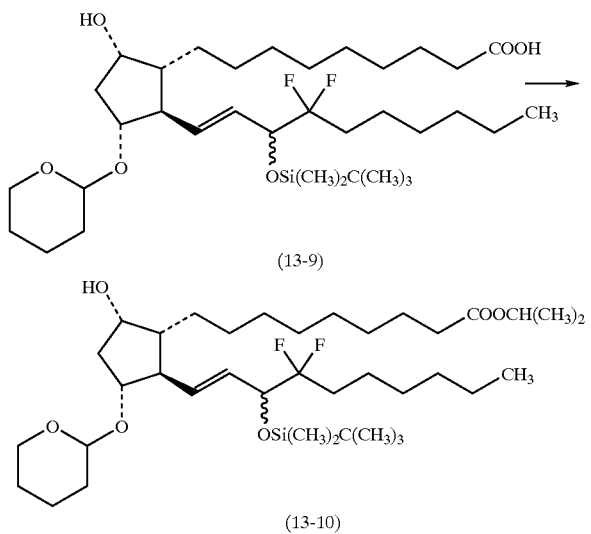

(13-9)

(13-10)

The compound (13-8)(3.11 g) was dissolved in ethanol (43 ml) and to this solution, 1N-sodium hydroxide aqueous solution (42.5 g) was added, and resultant mixture was stirred for 34 hours at room temperature. Using conventional treatment, 9-{2(R)-[4,4-difluoro-3(RS)-(t-butyldimethylsiloxy)dece-1-nyl]-5(R)-hydroxy-3(R)-(tetrahydropyranyloxy)cyclopentyl}nonanoic acid (13-9) was obtained.

The carboxylic acid (13-9) was dissolved in acetonitrile (16 ml) and to this solution, isopropyl iodide (1.69 ml) and DBU (2.54 ml) were added, and the mixture was stirred for 2 hours at 50–55° C. The crude product obtained by the conventional treatment was purified by silica gel chromatography (n-hexane/ethyl acetate=8/2) to give the titled compound (13-10).

Yield:2.60 g(89%, 2 reaction processes)

13-9)

Isopropyl 9-{2(R)-[4,4-difluoro-3(RS)-(t-butyldimethylsiloxy)dece-1-nyl]-3(R)-(tetrahydropyranyloxy)-5-oxocyclopentyl}nonanoate (13-11)

(13-11)

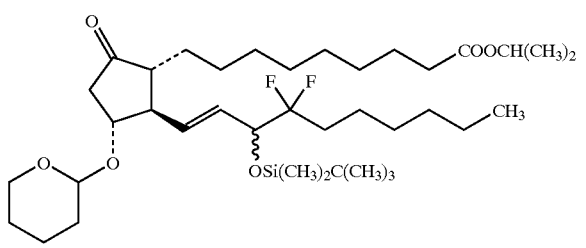

Oxalyl chloride (2M, in $CH_2Cl_2$, 2.28 ml) was diluted by dichloromethane (15 ml) and the solution was cooled to −78° C., to which the solution, DMSO (0.65 ml) was added and the mixture was stirred for 30 minutes. To this mixture, a solution (10 ml) of the compound (15-10)(1.57 g) in dichloromethane and then triethylamine (1.58 ml) were added, in which the mixture was subjected to Swan oxydation. The crude product obtained by the conventional treatment was purified by silica gel chromatography (n-hexane/ethyl acetate=85/15) to give the titled compound (13-11).

Yield:1.53 g(98%)

13-10)

Isopropyl 9-{2(R)-[4,4-difluoro-3(R)-hydroxydece-1-nyl]-3(R)-hydroxy-5-oxocyclopentyl}nonanoate (13-12)

(13-12)

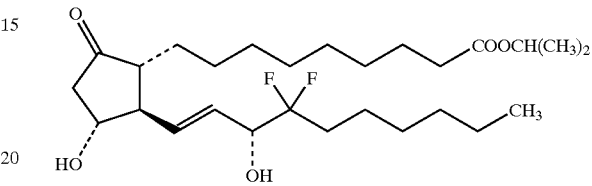

The compound (13-11)(0.28 g) was dissolved in acetonitrile(5.5 ml) and into this solution, 47% hydrofluoric acid was added, stirred for 3 hours at 0° C. and for 5 hours at room temperature. The crude product obtained by the conventional treatment was purified by silica gel chromatography (n-hexane/ethyl acetate=7/3–1/1) to give the titled compound (13-12).

Yield:0.061 g(31%)

N.m.r.($CDCl_3$) δ:0.88(3H,t,J=7.6 Hz), 1.22(6H,d,J=6.6 Hz), 1.25–2.85(30H,m), 3.48(2H,br), 4.07(1H,q,J=7.5 Hz), 4.26(1H,m), 4.99(1H,sept,J=6.6 Hz), 5.78(2H,m).

Mass. m/z:470($M^+$-$H_2O$), 451($M^+$-$H_2O$—F)

Rf.value: 0.35(silica gel 60, n-hexane/ethyl acetate=3/7)

Further, 0.071 g(36%) of 17 β-isomer was obtained.

Synthesis Example 14

The preparation of 2-decarboxy-2-(2-carboxyethyl)-13,14-dihydro-15-keto-$PGF_{2\alpha}$ isopropyl ester [IUPAC name: isopropyl (Z)-9-[(1R,2R,3R,5S)-3,5-dihydroxy-2-(3-oxooctyl)cyclopentyl]-7-nonenoate] (4-b)

(4-b)

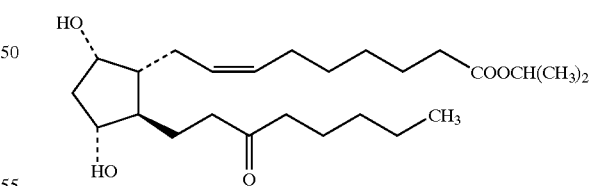

Except for using the compound(3-b) ($P_1$=tetrahydropyranyl, $P_2$=—$CH_2$—$CH_2$—, $X_1$=$X_2$=H, $R_2$-$R_3$=butyl, $P_3$=isopropyl), the titled compound (4-b) was obtained by the same way as Synthesis Example 1. The compound(4-b)(in the compound (4), $X_1$=$X_2$=H, $R_2$-$R_3$=butyl, $P_3$=isopropyl)

N.M.R.($CDCl_3$) δ:0.88(3H,t,J=7.5 Hz), 1.23(6H,d,J=6.0 Hz), 1.23–2.50(28H,m), 2.26(2H,t,J=7.5 Hz), 2.42(2H,t,J=7.5 Hz), 2.58(2H,t,J=7.5Hz), 2.85(1H,br,d), 3.88(1H,br), 4.17(1H,br), 5.00(1H,Sept,J=6.0 Hz), 5.41(2H,m).

Synthesis Example 15

The preparation of 2-decarboxy-2-(2-carboxyethyl)-13,14-dihydro-15-keto-16,16-difluoro-20-ethyl-PGE$_2$ isopropyl ester [IUPAC name: isopropyl (Z)-9-[(1R,2R,3R)-2-(4,4-difluoro-3-oxodecyl)-3-hydroxy-5-oxocyclopentyl]-7-nonenoate] (17-b)

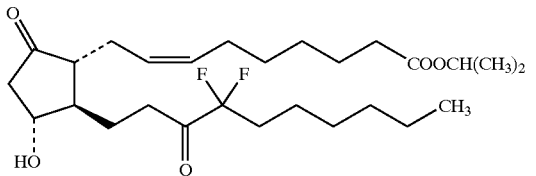

(17-b)

Except for using dimethyl(3,3-difluoro-2-oxononyl)phosphonate, the titled compound (17-b) was obtained by the same way as Synthesis Example 3. Compound (17-b)(in compound (17), $X_1=X_2=F$, $R_2–R_3=$hexyl, isopropyl ester)

N.M.R.(CDCl$_3$) δ:0.91(3H,t,J=7.5 Hz), 1.24(6H,d,J=6.0 Hz), 1.24–2.50(26H,m), 2.26(1H,dd,J=17.5 Hz, J=10.0 Hz), 2.28(2H,t, J=7.5 Hz), 2.62(1H,dd,J=17.5 Hz, J=6.5 Hz), 2.78(1H,br,s), 4.22(1H,m), 5.02(1H,Sept,J=6.0 Hz), 5.39 (2H,m).

Synthesis Example 16

The preparation of 2-decarboxy-2-(2-carboxyethyl)-13,14-dihydro-15-keto-20-ethyl-PGF$_{1\alpha}$ isopropyl ester [IUPAC name: isopropyl 9-[(1R,2R,3R,5S)-3,5-dihydroxy-2-(3-oxodecyl)cyclopentyl]-nonanoate] (16-1)

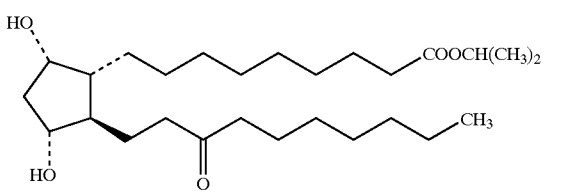

(16-1)

The compound (4-a) of Synthesis Example 1 was subjected to hydrogenation using 5%Pd—C and hydrogen gas in ethyl acetate and the resultant was purified on silica gel column to obtain the titled compound (16-1).

N.M.R.(CDCl$_3$) δ:0.89(3H,t,J=7.5 Hz), 1.23(6H,d,J=6.0 Hz), 1.27–2.03(29H,m), 1.18(2H,br,s), 2.26(2H,t,J=7.5 Hz), 2.41(2H,t, J=7.5 Hz), 2.56(2H,br,t,J=6.5 Hz), 2.66(2H,br,s), 3.91(1H,br,s), 4.20(1H,br,s), 5.00(1H,Sept,J=6.0 Hz).

Synthesis Example 17

The preparation of 2-decarboxy-2-(2-carboxyethyl)-13,14-dihydro-15-keto-16,16-difluoro-20-ethyl-PGF$_{2\alpha}$ isopropyl ester[IUPAC name: isopropyl Z-9-[(1R,2R,3R,5S)-3,5-dihydroxy-2-(4,4-difluoro-3-oxodecyl)cyclopentyl]-7-nonenoate] (32-b)

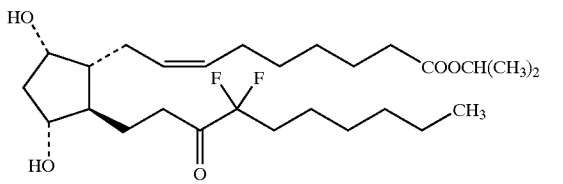

(32-b)

Except for using the compound (12-b)($X_1=X_2=F$, $P_1=$tetrahydropyranyl, $R_2–R_3=$hexyl in compound (12)) and isopropyl iodide for esterification, titled Compound (32-b) was obtained in the same way as Synthesis Example 7.

The compound (32-b)($X_1=X_2=F$, $R_2–R_3=$hexyl, $P_3=$isopropyl in the compound (32))

N.M.R.(CDCl$_3$) δ:0.89(3H,t,J=5Hz), 1.24(6H,d,J=6.0 Hz), 1.24–2.37(28H,m), 2.26(2H,t,J=7.0 Hz), 2.47(1H,dt,J=12.5Hz,J=7.5 Hz), 2.71(0.7H,m), 2.83(0.3H,m), 3.70(0.7H, m), 3.90(0.3H,br,s), 4.26(1H,br,s), 5.00(1H,Sept,J=6.0 Hz), 5.43(2H,m).

Synthesis Example 18

The preparation of 2-decarboxy-2-(2-carboxyethyl)-13,14-dihydro-15-keto-16,16-difluoro-20-ethyl-PGE$_1$ [IUPAC name: 9-[(1R,2R,3R)-3-hydroxy-5-oxo-2-(4,4-difluoro-3-oxodecyl)cyclopentyl]-nonanoic acid] (33-b)

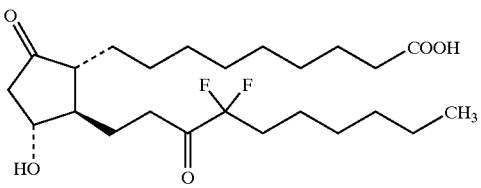

(33-b)

The titled compound (33-b) was obtained in the same way as Synthesis Example 8, except for using Compound (14-b) ($X_1=X_2=F$, $P_1=$tetrahydropyranyl, $R_2–R_3=$hexyl in the compound (14)).

Compound (33-b)($X_1=X_2=F$, $R_2–R_3=$hexyl in Compound (33)).

N.M.R.(CDCl$_3$) δ:0.90(3H,t,J=7.5 Hz), 1.06–1.14(38H, m), 2.25(1H,dd,J=17.5 Hz,J=11.5 Hz), 2.35(2H,t,J=7.5 Hz), 2.59(1H,dd, J=17.5 Hz,J=7.5 Hz), 4.19(1H,m).

Synthesis Example 19

The preparation of 2-decarboxy-2-(2-carboxyethyl)-13,14-dihydro-15-keto-16,16-difluoro-20-butyl-PGE$_1$ isopropyl ester [IUPAC name: isopropyl 9-[(1S,2S,3S)-3-hydroxy-5-oxo-2-(4,4-difluoro-3-oxododecyl)cyclopentyl]-nonanoate] (20-c)

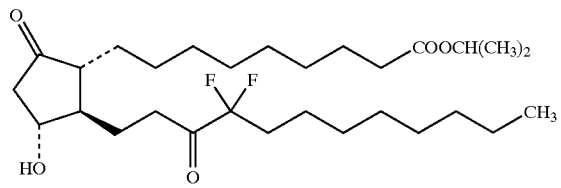

(20-c)

The titled compound (20-c) was obtained in the same way as Synthesis Example 4, except for using the compound (15-d) ($X_1=X_2=F$, $P_1=$tetrahydropyranyl, $R_2–R_3=$octyl $P_3=$isopropyl in the compound (15)).

The compound (20-c) ($X_1=X_2=F$, $R_2–R_3=$octyl, $P_3=$isopropyl in the compound (20)).

N.M.R.(CDCl$_3$) δ:0.89(3H,t,J=7.5 Hz), 1.23(6H,d,J=6.0 Hz), 1.23–2.15(34H,m), 2.24(1H,dd,J=17.5 Hz,J=10.0 Hz), 2.26(2H,t, J=7.5 Hz), 2.58(1H,dd,J=17.5 Hz,J=6.5 Hz), 2.88 (1H,br,s), 4.18(1H,m), 5.00(1H,Sept,J=6.0 Hz).

Synthesis Example 20

The preparation of 2-decarboxy-2-(2-carboxyethyl)-13,14-dihydro-15-keto-16,16-difluoro-20-isopropyl-PGE$_1$ isopropyl ester [IUPAC name: isopropyl 9-[(1R,2R,3R)-3-hydroxy-5-oxo-2-(4,4-difluoro-9-methyl-3-oxodecyl)cyclopentyl]-nonanoate] (20-d)

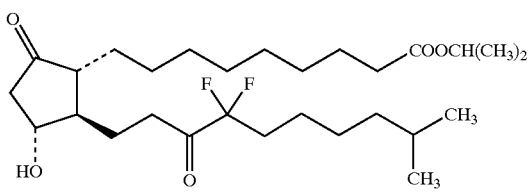

(20-d)

The titled compound (20-d) was obtained in the same way as Synthesis Example 4, except for using Compound (15-d) (X$_1$=X$_2$=F, P$_1$=tetrahydropyranyl, R$_2$–R$_3$=1-methylhexyl, P$_3$=isopropyl in the compound (15)).

Compound (20-d) (X$_1$=X$_2$=F, R$_2$–R$_3$=1-methylhexyl, P$_3$=isopropyl in the compound (20)).

N.M.R.(CDCl$_3$) δ:0.87(6H,d,J=7.0 Hz), 1.22(6H,d,J=6.0 Hz), 1.22–2.12(29H,m), 2.23(1H,dd,J=12.5 Hz,J=10.0 Hz), 2.24(2H,t,J=7.5 Hz), 2.56(1H,dd,J=17.5 Hz,J=7.5 Hz), 2.97 (1H,br,s), 4.17(1H,m), 4.99(1H,Sept,J=6.0 Hz).

Synthesis Example 21

The preparation of 2-decarboxy-2-(2-carboxyethyl)-13,14-dihydro-15-keto-16,16-difluoro-20-methoxy-PGE$_1$ isopropyl ester [IUPAC name: isopropyl 9-[(1R,2R,3R)-3-hydroxy-5-oxo-2-(4,4-difluoro-8-methoxy-3-oxooctyl)cyclopentyl]-nonanoate] (20-e)

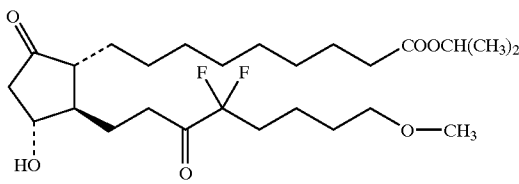

(20-e)

The titled compound (20-e) was obtained in the same way as Synthesis Example 4, except for using Compound (15-e) (X$_1$=X$_2$=F, P$_1$=tetrahydropyranyl, R$_2$–R$_3$=methoxybutyl, P$_3$=isopropyl in the compound (15)).

The compound (20-e) (X$_1$=X$_2$=F, R$_2$–R$_3$=methoxybutyl, P$_3$=isopropyl in the compound (20)).

N.M.R.(CDCl$_3$) δ:1.23(6H,d,J=6.0 Hz), 1.23–2.15(27H, m), 2.23(1H,dd,J=17.5 Hz,J=11.5 Hz), 2.24(2H,t,J=7.5 Hz), 2.57(1H,dd,J=17.5 Hz,J=7.5 Hz), 2.98(1H,br,s), 3.34(3H,s), 3.40(2H,m), 4.18(1H,m), 5.00(1H,Sept,J=6.0 Hz).

Synthesis Example 22

The preparation of 2-decarboxy-2-(2-carboxyethyl)-13,14-dihydro-15-keto-16,16-difluoro-19,20-bisnor-18-phenyl-PGE$_1$ isopropyl ester [IUPAC name: isopropyl 9-[(1R,2R,3R)-3-hydroxy-5-oxo-2-(4,4-difluoro-6-phenyl-3-oxohexyl)cyclopentyl]-nonanoate] (20-f)

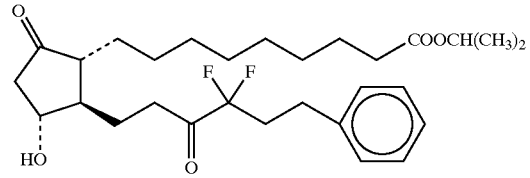

(20-f)

The titled compound (20-f) was obtained in the same way as Synthesis Example 41 except for using Compound (15-f) (X$_1$=X$_2$=F, P$_1$=tetrahydropyranyl, R$_2$–R$_3$=phenylethyl, P$_3$=isopropyl in the compound (15)).

Compound(20-f) (X$_1$=X$_2$=F, R$_2$–R$_3$=phenylethyl, P$_3$=isopropyl in the compound (20)).

N.M.R.(CDCl$_3$) δ:1.22(6H,d,J=6.0 Hz), 1.22–2.55(22H, m), 2.22 (1H,dd,J=16.5 Hz,J=12.5 Hz), 2.24(2H,t,J=7.5 Hz), 2.55(1H,dd, J=17.5 Hz,J=7.5 Hz), 2.88(2H,t,J=7.5 Hz), 3.17 (1H,br,s), 4.17(1H,m), 4.99(1H,Sept,J=6.0 Hz), 7.25(5H,m).

Synthesis Example 23

The preparation of 2-decarboxy-2-(2-carboxyethyl)-13,14-dihydro-15-keto-16,16-difluoro-20-ethyl-PGF$_{1\alpha}$ isopropyl ester [IUPAC name: isopropyl 9-[(1R,2R,3R,5S)-3,5-dihydroxy-2-(4,4-difluoro-3-oxodecyl)cyclopentyl]-nonanoate] (23-1)

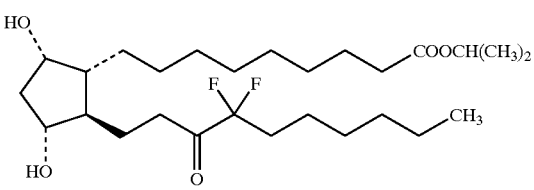

(23-1)

The compound (32-b) of Synthesis Example 17 was subjected to hydrogenation using 5%Pd-C and hydrogen gas in ethyl acetate and the resultant was purified on silica gel colmun to give the titled compound (23-1).

N.M.R.(CDCl$_3$) δ:0.90(3H,t,J=7.5 Hz), 1.23(6H,d,J=6.5 Hz), 1.26 –2.15(32H,m), 2.26(2H,t,J=7.5 Hz), 2.49(1H,dt, J=7.5 Hz,J=7.5 Hz), 2.66 (8H,br,s), 2.82(0.2H,br,t,J=6.0 Hz), 3.70(0.8H,q,J=6.8 Hz), 3.92 (0.2H,m), 4.24(1H,m), 5.00(1H,Sept,J=6.5 Hz).

Synthesis Example 24

The preparation of 2-decarboxy-2-(2-carboxyethyl)-15-keto-16,16-difluoro-20-methoxy-PGE$_1$ isopropyl ester [IUPAC name: isopropyl 9-[(1R,2R,3R)-3-hydroxy-5-oxo-2-(E-4,4-difluoro-8-methoxy-3-oxooct-1-enyl)cyclopentyl]-nonanoate] (24-1)

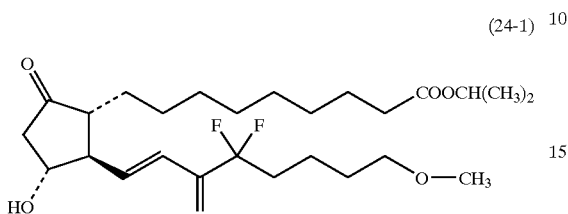

(24-1)

The titled compound (24-1) was obtained in the same way as Synthesis Example 11, except that the reaction was performed using the compound (11-8) of Synthesis Example 11 and dimethyl(3,3-difluoro-7-methoxyheptyl) phosphonate.

N.M.R.(CDCl$_3$) δ:1.23(6H,d,J=6.0 Hz), 1.23–1.44(9H, m), 1.44–1.80(9H,m), 1.90–2.30(3H,m), 2.25(2H,t,J=6.5 Hz), 2.32(1H,dd, J=17.5 Hz,J=7.5 Hz), 2.60–2.72(2H,m), 2.82(1H,dd,J=17.5 Hz,J=7.5 Hz), 3.33(3H,s), 3.39(2H,t,J= 5.0 Hz), 4.25(1H,q,J=7.5 Hz), 5.00(1H, Sept,J=6.0 Hz), 6.73(1H,dd,J=15.0 Hz), 7.12(1H,dd,J=15.0 Hz,J=7.5 Hz).

Synthesis Example 25

The preparation of 2-decarboxy-2-(2-carboxyethyl)-13,14-dihydro-20-ethyl-PGF$_{2\alpha}$ isopropyl ester [IUPAC name: isopropyl Z-9-[(1R,2R, 3R,5S)-3,5-dihydroxy-2-(3(S)-hydroxydecyl)cyclopentyl]-7-nonenoate] (25-1)

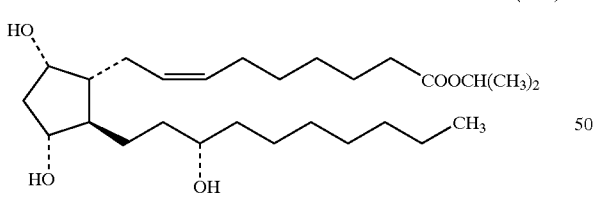

(25-1)

The compound (28-b) (X$_1$=X$_2$=H, P$_1$=P$_6$= tetrahydropyranyl, R$_2$–R$_3$=hexyl, P$_3$=isopropyl in the compound (28)) was subjected to deprotection in solvent of acetic acid-water-THF and then the resultant was purified on silica gel colmun to give the titled compound.

N.M.R.(CDCl$_3$) δ:0.90(3H,t,J=7.5 Hz), 1.23(6H,d,J=6.0 Hz), 1.23–1.80(26H,m), 1.89(2H,t,J=2.5 Hz), 2.10(2H,m), 2.20(1H,d, J=5.0 Hz), 2.27(2H,t,J=5.0 Hz), 2.30(1H,m), 2.62(1H,d,J=7.5 Hz), 3.64(1H,m), 3.98(1H,m), 4.20(1H,m), 5.01(1H,Sept,J=6.0 Hz), 5.44(2H,m ).

Synthesis Example 26

The preparation of 2-decarboxy-2-(2-carboxyethyl)-13,14-dihydro-15-keto-16,16-difluoro-20-ethyl-Δ$^2$-PGE$_1$ isopropyl ester [IUPAC name: isopropyl E-9-[(1R,2R,3R)-3-hydroxy-5-oxo-2-(4,4-difluoro-3-oxodecyl)cyclopentyl]-2-nonenoate] (26-4)

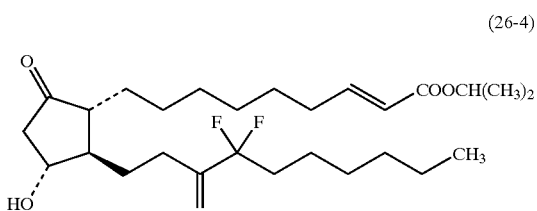

(26-4)

26-1)

Isopropyl 9-[(1R,2R,3R,5S)-3-tetrahydropyranyloxy-5-hydroxy-2-(4,4-difluoro-3(RS)-hydroxydecyl)cyclopentyl]-2(RS)-phenylselenyl nonanoate (26-1)

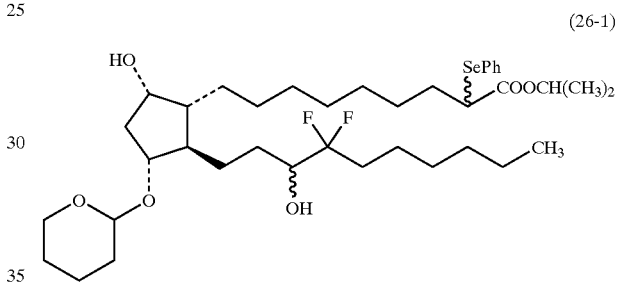

(26-1)

The compound (18-b) (X$_1$=X$_2$=F, P$_1$=tetrahydropyranyl, R$_2$–R$_3$=hexyl, P$_3$=isopropyl in the compound (18)) (0.632 g) was reacted using lithium diisopropylamide (LDA) and diphenyldiselenide in THF to give the compound (26-1).

Yield: 0.518 g (65%)

26-2)

Isopropyl E-9-[(1R,2R,3R,5S)-3-tetrahydropyranyloxy-5-hydroxy-2-(4,4-difluoro-3(RS)-hydroxydecyl)cyclopentyl]-2-nonenoate] (26-2)

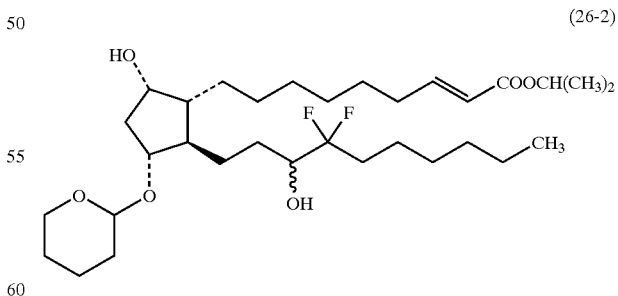

(26-2)

The compound (26-1) was reacted using 31% hydrogen peroxide in mixture of ethyl acetate-methanol and the resultant was purified on silica gel column to give thecompound (26-2).

Yield: 0.393 g (76%).

26-3)
Isopropyl E-9-[(1R,2R,3R)-3-tetrahydropyranyloxy-5-oxo-2-(4,4-difluoro-3-oxodecyl)cyclopentyl]-2-nonenoate] (26-3)

(26-3)

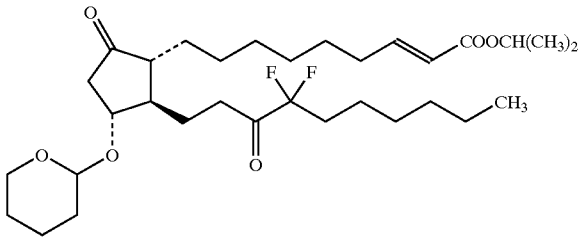

The compound (26-2) was subjected to Swan oxydation and the resultant was purified on silica gel column to give the compound (26-3).

Yield: 0.318 g (81%)

26-4)
Isopropyl E-9-[(1R,2R,3R)-3-hydroxy-5-oxo-2-(4,4-difluoro-3-oxodecyl)cyclopentyl]-2-nonenoate] (26-4)

The compound (26-3) was subjected to deprotection in the mixture of acetic acid-water-THF and then the resultant was purified on silica gel column to give the titled compound (26-4).

Yield: 0.177 g (65%)

N.M.R.(CDCl$_3$) δ:0.90(3H,t,J=7.5 Hz), 1.27(6H,d,J=6.0 Hz), 1.27–2.10(27H,m), 2.16(1H,t,J=6.5 Hz), 2.20(1H,br), 2.24(1H, dd,J=17.5 Hz,J=11.0 Hz), 2.59(1H,dd,J=17.5 Hz,J=7.5 Hz), 2.71(1H, br,s), 4.18(1H,m), 5.06(1H,Sept,J=6.0 Hz), 5.78(1H,d,J=16.0 Hz), 6.94(1H,dt,J=17.5 Hz,J=7.0 Hz).

Synthesis Example 27

The preparation of 2-decarboxy-2-(2-carboxyethyl)-13,14-dihydro-15-dehydroxy-20-ethyl-PGF$_{2\alpha}$ isopropyl ester [IUPAC name: isopropyl Z-9-[(1R,2R,3R,5S)-3,5-dihydroxy-2-decylcyclopentyl]-7-nonenoate] (27-6)

(27-6)

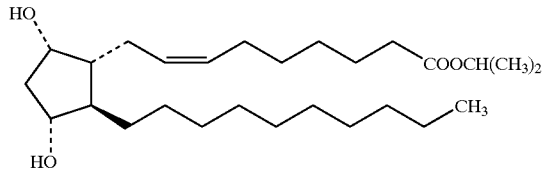

27-1)
(1S,5R,6R,7R)-7-benzoyloxy-6-[3(RS)-imidazoylthiocarbonyloxydecyl]-2-oxabicyclo[3.3.0]octane-3-on (27-1)

(27-1)

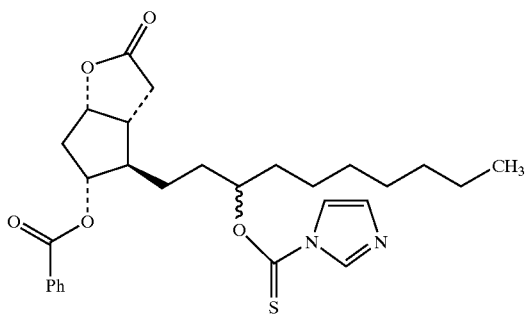

The compound (12-c) (X$_1$=X$_2$=H, P$_1$=phenyl, R$_2$–R$_3$=hexyl, in the compound (12)) (0.6768 g) was reacted with 1,1'-thiocarbonyl imidazole in 1,2-dichloromethane and the resultant was purified on silica gel column to give the compound (27-1).

Yield: 0.7959 g (92.4%)

27-2)
(1S,5R,6R,7R)-7-benzoyloxy-6-decyl-2-oxabicyclo [3.3.0]octane-3-one(27-2)

(27-2)

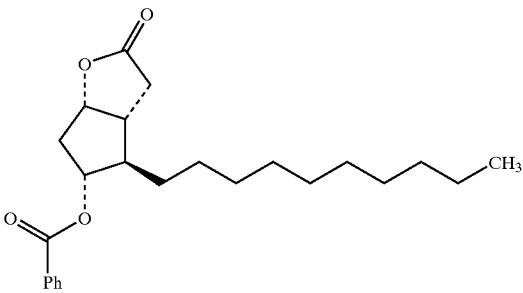

The compound (27-1) was reacted with tributyltin hydride in toluen and the resultant was purified on silica gel column to give the compound (27-2).

Yield: 0.5688 g (94.8%)

27-3)
(1S,5R,6R,7R)-6-decyl-7-hydroxy-2-oxabicyclo[3.3.0] octane-3-one (27-3)

(27-3)

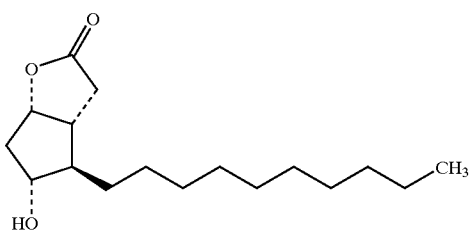

The compound (27-2) was reacted with potassium carbonate in dry methanol and the resultant was purified on silica gel column to give Compound (27-3).

Yield: 0.3420 g (82.3%)

27-4)
[1S,3(RS),5R,6R,7R]-6-decyl-7-hydroxy-2-oxabicyclo [3.3.0]octane-3-ol (27-4)

(27-4)

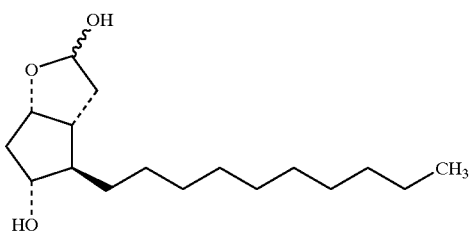

The compound (27-3) was reacted with DIBAL-H in toluen to give the compound (27-4). Yield: 0.2304 g (66.9%). 0.0940 g of the compound (27-3) was recovered, which was reacted in the same-way to give 0.0947 g of the compound (27-4).

Total yield: 0.3251 g.

27-5)

Z-9-[(1R,2R,3R,5S)-3,5-dihydroxy-2-decylcyclopentyl]-7-nonenoic acid (27-5)

(27-5)

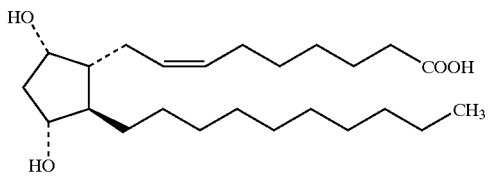

The compound (27-4) was reacted with the ylide prepared from the compound (e) of Synthesis Example 1 to give the compound (27-5).

Yield: 0.9246 g 27-6)

Isopropyl Z-9-[(1R,2R,3R,5S)-3,5-dihydroxy-2-decylcyclopentyl]-7-nonenoate (27-6)

The compound (27-5) was reacted with isopropyl iodide and DBU in dry acetonitrile and the resultant was purified on silica gel column to give the titled compound (27-6).

Yield: 0.3860 g (77.0%)

N.M.R.(CDCl$_3$) δ:0.88(3H,t,J=7.5 Hz), 1.23(6H,d,J=6.5 Hz), 1.25–1.50(23H,m), 1.50–1.75(3H,m), 1.86(2H,m), 2.10(2H,q, J=5.1Hz), 2.27(4H,quint,J=7.5 Hz), 2.41(1H,br), 2.67(1H,br), 3.94(1H,br), 4.18(1H,br), 5.00(1H,Sept,J=6.5 Hz), 5.42(2H,m).

Synthesis Example 28

The preparation of 2-decarboxy-2-(4-carboxybutyl)-13,14-dihydro-15-keto-20-ethyl-PGF$_{2\alpha}$ isopropyl ester [IUPAC name: isopropyl Z-11-[(1R,2R,3R,5S)-3,5-dihydroxy-2-(3-oxodecyl)cyclopentyl]-9-undecenoate] (28-4)

(28-4)

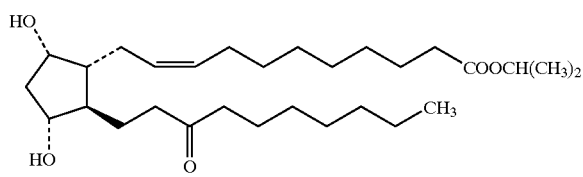

Preparation of the raw material compounds (8-carboxyoctyl)triphenylphosphonium bromide (h)

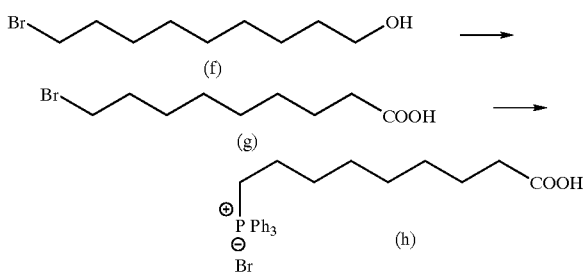

9-Bromononyl alcohol (f) (3.347 g) was reacted with sodium metaperiodate and ruthenium chloride in the mixture of carbon tetrachloride, acetonitrile and water to give 9-bromo nonanoic acid (g).

Yield: 2.632 g (74.0%)

9-Bromononanoic acid (g) (2.6103 g) was reacted with triphenylphosphine in acetonitrile and (8-carboxyoctyl) triphenylphosphonium bromide (h) was obtained.

Yield: 4.936 g (89.9%)

Preparation of objective compound 28-1)

Z-11-[(1R,2R,3R,5S)-3,5-dihydroxy-2-(3,3-ethylenedioxydecyl)cyclopentyl]-9-undecenoic acid] (28-1)

(28-1)

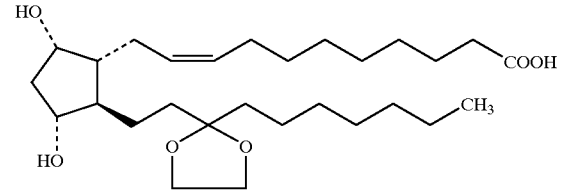

[1S,3(RS),5R,6R,7R]-6-(3,3-ethylenedioxydecyl-7-tetrahydropyranyloxy-2-oxabicyclo[3.3.0]octane-3-ol (1-a) (0.5600 g) of Synthesis Example 1 was reacted with ylide preparated from (8-carboxyoctyl)triphenylphosphonium bromide (h) to give the compound (28-1) in the same way as 1-1) of Synthesis Example 1.

Yield: 2.914 g 28-2)

Isopropyl Z-11-[(1R,2R,3R,5S)-3,5-dihydroxy-2-(3,3-ethylenedioxydecyl)cyclopentyl]-9-undecenoate (28-2)

(28-2)

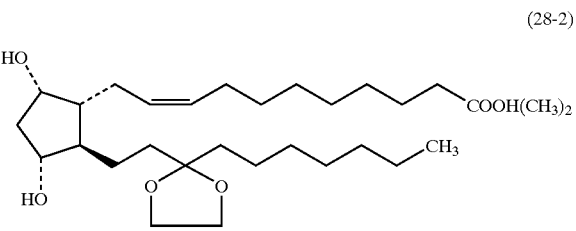

The compound (28-1) (2.914 g) was reacted with isopropyl iodide and DBU in acetonitrile and the resultant was subjected to silica gel column purification to give the compound (28-2).

Yield: 0.4834 g (57.6%)

28-3)

Isopropyl Z-11-[(1R,2R,3R,5S)-3,5-dihydroxy-2-(3-oxodecyl)cyclopentyl]-9-undecenoate The compound (28-2) (0.4834 g) was dissolved in the mixture of acetic acid-THF-water and hold for two hours at 50° C. The resultant was purified on silica gel column to give the titled compound (28-4).

Yield: 0.3593 g (81.1%)

N.M.R.(CDCl$_3$) δ:0.88(3H,t,J=7.5 Hz), 1.23(6H,d,J=6.5 Hz), 1.25–1.95(26H,m), 1.95–2.19(3H,m), 2.27(2H,t,J=7.5 Hz), 2.19–2.35(2H,m), 2.41(2H,t,J=7.5 Hz), 2.57(2H,dt,J= 7.5 Hz,J=1.5 Hz), 2.67(1H,d,J=7.5 Hz), 3.89(1H,m), 4.19 (1H,m), 5.00(1H,Sept,J=6.5 Hz), 5.42(2H,m).

Test Example 1

Japanese white male rabbit (2.5 to 2.8 kg body weight) was used, and $10^{-6}$ μl of endothelin-1 (ET-1: Peptide Kenkyusho) was administered into the corpus vitreum of the rabbit under urethane anesthesia, whereby circulation disorder of the optic disk was induced.

To the rabbit was once administered 35 μl of a physiological saline containing 0.006% of the test substance by means of ophthalmic administration 15 minutes before administration of the ET-1. To the control group was administered the same amount of physiological saline only.

Time-varying blood flow of the optic disk was measured by the use of a hydrogen clearance type tissue blood flowmeter (manufactured by Biomedical Science), and a relative blood flow of optic disk wherein the blood flow of optic disk prior to administration of ET-1 was considered to be 100% was determined.

Measurement of blood flow of optic disk was conducted as described hereinafter. An eyeball of a rabbit under urethane anesthesia was fixed at a slightly supravergent position, then, an acicular different electrode was inserted into the corpus vitreum from sclera on the side of more posterior pole of the eyeball than that of eyeball ring portion, and further inserted in the central portion of the optic disk (depth of insertion: 0.7 mm) under direct vision by employing a Vitrectomie lens. On one hand, an indifferent electrode was inserted under the skin of the head, and fixed thereto. The rabbit was allowed to inhale air containing 4% $H_2$ for 5 minutes under spontaneous respiration in accordance with open masking method, and blood flow of optic disk tissue (ml/minute/100 g tissue) was calculated from attenuation of hydrogen concentration in the tissue after stopping hydrogen inhalation by the use of hydrogen clearance type tissue blood flowmeter (manufactured by Biomedical Science).

The results are shown in Table 1 wherein elapsed time (minutes) was measured from the start 0 minute (at the time of administering ET-1).

TABLE 1

| Test Substance | Number of Example (n) | Relative Blood Flow of Optic Disk (Average ± S.E.: %) | | | | |
|---|---|---|---|---|---|---|
| | | 30 | 60 | 120 | 180 | 240 (min.) |
| Control | 6 | 83.1 ± 5.0 | 75.9 ± 5.4 | 58.9 ± 8.1 | 55.3 ± 6.1 | 48.0 ± 2.4 |
| Test Substance 1 | 3 | 109.0* ± 4.9 | 103.8* ± 1.6 | 89.3* ± 1.2 | 87.5* ± 5.1 | 79.5** ± 6.2 |

**P < 0.01, *P < 0.05 (Comparison with control group by Student's t-test)

Test Substance 1: 2-decarboxy-2-(2-carboxyethyl)-13,14-dihydro-15-keto-20-ethyl-$PGF_{2\alpha}$ isopropyl ester (the compound in synthesis example 1)

It can be seen from the above results that since the test substance 1 being the compound according to the present invention suppressed significantly circulation disorder of optic disk induced by endothelin, the substance had extremely strong endothelin antagonistic action.

Test Example 2

The same test as that of Test Example 1 was conducted except that the test substance 2 described hereunder was used as the substance to be tested.

The results are shown in Table 2.

TABLE 2

| Test Substance | Number of Example (n) | Relative Blood Flow of Optic Disk (Average ± S.E.: %) | | |
|---|---|---|---|---|
| | | 60 | 150 | 240 (min.) |
| Control | 6 | 75.9 ± 5.4 | 57.6 ± 4.3 | 48.0 ± 2.4 |
| Test Substance 2 | 3 | 96.2 ± 5.6 | 75.2 ± 6.9 | 72.9** ± 9.4 |

**P < 0.01 (Comparison with control group by Student's t-test)

Test Substance 2: 2-decarboxy-2-(2-carboxyethyl)-13,14-dihydro-15-keto-16,16-difluoro-20-ethyl-$PGE_1$ isopropyl ester (compound in synthesis example 9)

Test Example 3

The same test as that of Test Example 1 was conducted except that the test substance 3 described hereunder was used as the substance to be tested.

The results are shown in Table 3.

TABLE 3

| Test Substance | Number of Example (n) | Relative Blood Flow of Optic Disk (Average ± S.E.: %) | |
|---|---|---|---|
| | | 210 | 240 (min.) |
| Control | 6 | 54.3 ± 6.5 | 48.0 ± 2.4 |
| Test Substance 3 | 3 | 80.6 ± 8.1 | 74.6 ± 6.0 |

Test Substance 3: 2-decarboxy-2-(2-carboxyethyl)-13,14-dihydro-15-keto-16,16-difluoro-20-ethyl-$PGF_1$ isopropyl ester (compound in synthesis example 23)

Test Example 4

The same test as that of Test Example 1 was conducted except that the test substance 4 described hereunder was used as the substance to be tested.

The results are shown in Table 4.

TABLE 4

| Test Substance | Number of Example (n) | Relative Blood Flow of Optic Disk (Average ± S.E.: %) | | | | |
|---|---|---|---|---|---|---|
| | | 30 | 60 | 120 | 180 | 240 (min.) |
| Control | 8 | 81.8 ± 4.0 | 75.3 ± 3.8 | 60.5 ± 6.3 | 55.3 ± 4.9 | 49.3 ± 2.8 |
| Test Substance 4 | 4 | 114.9** ± 3.0 | 92.2 ± 8.7 | 75.7 ± 5.8 | 62.7* ± 8.0 | 66.5* ± 6.8 |

**$P < 0.01$, *$P < 0.05$ (Comparison with control group by Student's t-test)

Test Substance 4: 2-decarboxy-2-(2-carboxyethyl)-13,14-dihydro-15-keto-16,16-difluoro-20-ethyl-PGF$_{2\alpha}$ isopropyl ester (compound in synthesis example 17)

Test Example 5

The same test as that of Test Example 1 was conducted except that the test substance 5 described hereunder was used as the substance to be tested.

The results are shown in Table 5.

TABLE 5

| Test Substance | Number of Example (n) | Relative Blood Flow of Optic Disk (Average ± S.E.: %) | | | | |
|---|---|---|---|---|---|---|
| | | 30 | 60 | 120 | 180 | 240 (min.) |
| Control | 8 | 81.8 ± 4.6 | 75.3 ± 3.8 | 60.5 ± 6.3 | 55.3 ± 4.9 | 49.3 ± 2.8 |
| Test Substance 5 | 4 | 96.7 ± 4.2 | 93.8* ± 4.4 | 80.8 ± 2.9 | 86.5** ± 2.9 | 80.2** ± 5.3 |

**$P < 0.01$, *$P < 0.05$ (Comparison with control group by Student's t-test)

Test Substance 5: 2-decarboxy-2-(2-carboxyethyl)-13,14-dihydro-15-dehydroxy-20-ethyl-PGF$_{2\alpha}$ isopropyl ester (compound in synthesis example 27)

Test Example 6

The same test as that of Test Example 1 was conducted except that the test substance 6 described hereunder was used as the substance to be tested.

The results are shown in Table 6.

TABLE 6

| Test Substance | Number of Example (n) | Relative Blood Flow of Optic Disk (Average ± S.E.: %) | | | | |
|---|---|---|---|---|---|---|
| | | 30 | 60 | 120 | 180 | 240 (min.) |
| Control | | 81.8 ± 4.6 | 75.3 ± 3.8 | 60.5 ± 6.3 | 55.3 ± 4.9 | 49.3 ± 2.8 |
| Test Substance 6 | | 96.6 ± 7.1 | 96.9* ± 8.9 | 89.9* ± 7.3 | 83.0** ± 4.3 | 74.8** ± 5.5 |

**$P < 0.01$, *$P < 0.05$ (Comparison with control group by Student's t-test)

Test Substance 6: 2-decarboxy-2-(2-carboxyethyl)-13,14-dihydro-15-keto-PGF$_{2\alpha}$ isopropyl ester (compound in synthesis example 14)

Test Example 7

The same test as that of Test Example 1 was conducted except that the test substance 7 described hereunder was used as the substance to be tested.

The results are shown in Table 7.

TABLE 7

| Test Substance | Number of Example (n) | Relative Blood Flow of Optic Disk (Average ± S.E.: %) | |
|---|---|---|---|
| | | 90 | 180 (min.) |
| Control | 8 | 66.0 ± 5.0 | 55.3 ± 4.9 |
| Test Substance 7 | 4 | 75.4 ± 7.0 | 61.0 ± 5.6 |

What is claimed is:
1. A compound represented by the general formula (III):

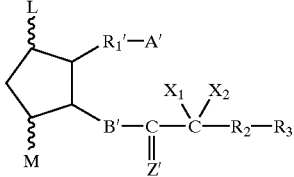

(III)

wherein L and M are hydrogen, hydroxy, halogen, lower alkyl, hydroxy(lower)alkyl, or oxo wherein at least one of L and M is a group other than hydrogen, and the five-membered ring may have at least one double bond;

A' is —COOH, or its finctional derivatives;

B' is —CH$_2$—CH$_2$—;

Z' is

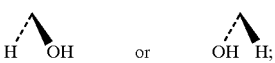

$X_1$ and $X_2$ are hydrogen, lower alkyl, or halogen wherein at least one of $X_1$ and $X_2$ is a halogen;

$R_1'$ is a divalent saturated or unsaturated aliphatic hydrocarbon residue having 8 carbon atoms, which is unsubstituted or substituted by halogen, oxo, or aryl;

$R_2$ is a single bond or lower alkylene; and $R_3$ is lower alkyl, lower alkoxy, cyclo(lower)alkyl, aryl, or aryloxy.

2. A compound represented by the general formula (IV):

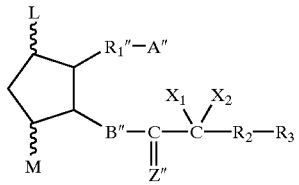

(IV)

wherein L and M are hydrogen, hydroxy, halogen, lower alkyl, hydroxy(lower)alkyl, or oxo wherein M is a group other than hydrogen, and the five-membered ring may have at least one double bond;

A" is —COOH, or its functional derivatives;

B" is —CH$_2$—CH$_2$—, or —CH=CH—;

Z" is

$X_1$ and $X_2$ are independently hydrogen, lower alkyl, or halogen;

$R_1'$ is a divalent saturated or unsaturated aliphatic hydrocarbon residue having 8 carbon atoms, which is unsubstituted or substituted by halogen, oxo, or aryl;

$R_2$ is a single bond or lower alkylene; and $R_3$ is lower alkyl, lower alkoxy, cyclo(lower)alkyl, aryl, or aryloxy.

3. A compound represented by the general formula (V):

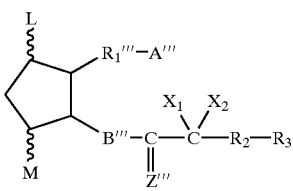

(V)

wherein L and M are hydrogen, hydroxy, halogen, lower alkyl, hydroxy(lower)alkyl, or oxo wherein M is a group other than hydrogen, and the five-membered ring may have at least one double bond;

A''' is —COOH, or its functional derivatives;

B''' is —CH$_2$—CH$_2$—, or —CH=CH—;

Z''' is

$X_1$ and $X_2$ are independently hydrogen, lower alkyl, or halogen;

$R_1'''$ is a divalent saturated or unsaturated aliphatic hydrocarbon residue having 10 carbon atoms, which is unsubstituted or substituted by halogen, oxo, or aryl;

$R_2$ is a single bond or lower alkylene; and $R_3$ is lower alkyl, lower alkoxy, cyclo(lower)alkyl, aryl, or aryloxy.

4. A compound according to claim 1, in which L and M are hydroxy or oxo.

5. A compound according to claim 2, in which L and M are hydroxy or oxo.

6. A compound according to claim 3, in which L and M are hydroxy or oxo.

* * * * *

UNITED STATES PATENT AND TRADEMARK OFFICE
CERTIFICATE OF CORRECTION

PATENT NO.    : 6,452,039 B1                                           Page 1 of 1
DATED         : September 17, 2002
INVENTOR(S)   : Ryuji Ueno It is certified that error appears in the above-identified patent and that said Letters Patent is hereby corrected as shown below:

<u>Title page,</u>
Please insert the following:

-- [73]  Assignee: R-Tech Ueno, Ltd., Osaka (JP) --

Signed and Sealed this

Twenty-second Day of April, 2003

JAMES E. ROGAN
*Director of the United States Patent and Trademark Office*